US011325904B2

(12) United States Patent
John et al.

(10) Patent No.: US 11,325,904 B2
(45) Date of Patent: May 10, 2022

(54) TROPINOL ESTERS AND RELATED COMPOUNDS TO PROMOTE NORMAL PROCESSING OF APP

(75) Inventors: Varghese John, San Francisco, CA (US); Dale E. Bredesen, Novato, CA (US)

(73) Assignee: BUCK INSTITUTE FOR RESEARCH ON AGING, Novato, CA (US)

(*) Notice: Subject to any disclaimer, the term of this patent is extended or adjusted under 35 U.S.C. 154(b) by 0 days.

(21) Appl. No.: 14/235,405

(22) PCT Filed: Aug. 1, 2012

(86) PCT No.: PCT/US2012/049223
§ 371 (c)(1),
(2), (4) Date: Aug. 13, 2014

(87) PCT Pub. No.: WO2013/019901
PCT Pub. Date: Feb. 7, 2013

(65) Prior Publication Data
US 2014/0364451 A1   Dec. 11, 2014

Related U.S. Application Data

(60) Provisional application No. 61/514,381, filed on Aug. 2, 2011.

(51) Int. Cl.
*C07D 453/02* (2006.01)
*C07D 451/12* (2006.01)
*A61K 31/439* (2006.01)
*A61K 31/444* (2006.01)
*A61K 45/06* (2006.01)

(52) U.S. Cl.
CPC .......... *C07D 453/02* (2013.01); *A61K 31/439* (2013.01); *A61K 31/444* (2013.01); *A61K 45/06* (2013.01); *C07D 451/12* (2013.01)

(58) Field of Classification Search
CPC ................................................... C07D 453/02
See application file for complete search history.

(56) References Cited

U.S. PATENT DOCUMENTS

| 4,486,441 A * | 12/1984 | Fozard et al. ................ 514/304 |
| 4,585,866 A * | 4/1986 | Fozard et al. ................ 546/129 |
| 5,434,161 A | 7/1995 | Becker et al. |
| 2002/0173511 A1 | 11/2002 | Wurtman et al. |
| 2005/0245504 A1 | 11/2005 | Corbett et al. |
| 2011/0178119 A1 | 7/2011 | Konradi et al. |

FOREIGN PATENT DOCUMENTS

WO   WO 2013/019901 A2   2/2013

OTHER PUBLICATIONS

Hibert "Conformation-Activity Relationship Study of 5-HT3 Receptor Antagonists and a Definition of a Model for This Receptor Site" Journal of Medicinal Chemistry 1990, 33, 1594-1600.*
Francis P. T. in Progress in Alzheimer's and Parkinson's Disease Plennum New York: 1998, p. 854.*
Hodges "Comparison of the effects of the 5-HT3 receptor antagonists WAY-100579 and ondansetron on spatial learning in the water maze in rats with excitotoxic lesions of the forebrain cholinergic projection system." Psychopharmacology (1996) 125:146-161.*
Back et. al. "Design, synthesis and SAR of potent statine-based BACE-1 inhibitors: Exploration of P1 phenoxy and benzyloxy residues" Bioorganic & Medicinal Chemistry 2008, 16, 9471-9486.*
Hook V. Y.H. "Neuroproteases in Peptide Neurotransmission and Neurodegenerative Diseases Applications to Drug Discovery Research" Biodrugs 2006, 20, 105-119.*
Jhee et. al. "B-amyloid therapies in Alzheimer's disease" Expert Opinion on Investigational Drugs 2001, 10, 593-605.*
Grazia D'Onofrio discusses some related therapies, "Advances in the identification of g-secretase inhibitors for the treatment of Alzheimer's disease" Expert Opinion on Investigational Drugs 2012, 7, 20-37.*
Ringman "Increased Prevalence of Significant Recurrent Headache in Preclinical Familial Alzheimer's Disease Mutation Carriers" Dement Geriatr Cogn Disord 2008;25:380-384 (abstract only).*
Beaumont "Design of Ester Prodrugs to Enhance Oral Absorption of Poorly Permeable Compounds: Challenges to the Discovery Scientist" Current Drug Metabolism, 2003, 4, 461-485.*
Rautio et. al. "Prodrugs: design and clinical Applications" Nature Reviews Drug Discovery 2008, 7, 255-270.*
Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Torpy JAMA patient page. "Mild cognitive impairment." JAMA 2009;302:452.*
Sperling "Toward defining the preclinical stages of Alzheimer's disease: Recommendations from the National Institute on Aging-Alzheimer's Association workgroups on diagnostic guidelines" Alzheimer's & Dementia 7 (2011) 280-292.*

(Continued)

*Primary Examiner* — David K O'Dell
(74) *Attorney, Agent, or Firm* — Harness Dickey & Pierce P.L.C.

(57) ABSTRACT

In various embodiments, compositions and methods are provided for treatment and/or prevention of amyloidogenic diseases. In certain embodiments, the methods entail administering an effective amount of a tropinol ester to a subject in need thereof for prophylactic or therapeutic effect. The methods are particularly useful for prophylactic and therapeutic treatment of Alzheimer's disease. In certain embodiments, methods of reducing the risk, lessening the severity, or delaying the progression or onset of a disease characterized by beta-amyloid deposits in the brain of a mammal are also provided. In certain embodiments, methods of directly or indirectly inhibiting the C-terminal cleavage of APP resulting in the formation of APP-C31 peptide and APPneo (AP-P664) in a mammal are provided.

7 Claims, 7 Drawing Sheets

Specification includes a Sequence Listing.

(56) References Cited

OTHER PUBLICATIONS

Mullane "Alzheimer's therapeutics: Continued clinical failures question the validity of the amyloid hypothesis—but what lies beyond?" Biochemical Pharmacology 85 (2013) 289-305.*
Luczkowski "'No screams and cries will convince us that white is white and black is black', an ode to the defenders of amyloid cascade hypothesis of Alzheimer's disease." Coordination Chemistry Reviews (2016), 327-328, 35-42.*
Herrup "The case for rejecting the amyloid cascade hypothesis" Nature Neuroscience (2015), 18(6), 794-799.*
Meyer "Reversible Cognitive Decline Accompanies Migraine and Cluster Headaches" Headache Sep. 2000, vol. 40, Issue 8, pp. 638-646 (abstract only).*
Atkins, "The clinical utility of gene testing for Alzheimer's disease" Neurology International 2011; vol. 3:e1.*
Brouwers "Molecular genetics of Alzheimer's disease: An update" Annals of Medicine, 2008, 40, 562-583.*
Dysken "Ondansetron in the treatment of cognitive decline in Alzheimer dementia" The American Journal of Geriatric Psychiatry; Mar./Apr. 2002; 10, 2; p. 212-215.*
Ban "Blockade of 5-HT3 receptor with MDL72222 and Y25130 reduces β-amyloid protein (25-35)-induced neurotoxicity in cultured rat cortical neurons." European Journal of Pharmacology 520 (2005) 12-21.*
Edink "Fragment Growing Induces Conformational Changes in Acetylcholine-Binding Protein: A Structural and Thermodynamic Analysis" Journal of the American Chemical Society, Published: Feb. 15, 2011, 133, 5363-5371.*
Hibbs, "Structural determinants for interaction of partial agonists with acetylcholine binding protein and neuronal .alpha.7 nicotinic acetylcholine receptor." 2009 EMBO Journal, 28(19), 3040-3051.*
Bitner "In vivo pharmacological characterization of a novel selective .alpha.7 neuronal nicotinic acetylcholine receptor agonist ABT-107: preclinical considerations in Alzheimer's disease." Journal of Pharmacology and Experimental Therapeutics, 2010, 334(3), 875-886.*
Mousavi, M., "Nicotinic receptor agonists and antagonists increase sAPPa secretion and decrease Aβ levels in vitro." Neurochem. Int. 2009, 54, 237-244.*
PCT Invitation to Pay Additional Fees and, Where Applicable, Protest Fee dated Nov. 14, 2012 issued in PCT/US12/49223.
PCT International Search Report and Written Opinion dated Jan. 17, 2013 issued in PCT/US12/49223.
PCT International Preliminary Report on Patentability and Written Opinion dated Feb. 13, 2014 issued in PCT/US12/49223.
Australian Patent Examination Report No. 1 dated Jan. 28, 2015 issued in Australian Patent Application No. 2012290116.
Saunders et al. (1987) "Synthesis and Characterization of All Four Isomers of the Muscarinic Agonist 2'-Methylspiro[1-azabicyclo[2.2.2]octane-3,4'-[1,3]dioxolane]", *Journal of Medicinal Chemistry*, 30(6):969-975.
Australian Patent Examination Report No. 1 dated Nov. 20, 2017 issued in Australian Patent Application No. 2017200543.
Alzheimer's Association Statement—BAN2401 Phase 2 Data Released at AAIC 2018 (CHICAGO, Jul. 25, 2018), 2 pages.
Dysken et al., (2002) "Ondansetron in the Treatment of Cognitive Decline in Alzheimer Dementia," *American Journal of Geriatric Psychiatry*, 10(2):212-5 (Abstract only—1 page).

\* cited by examiner

TROPINOL ESTERS AND RELATED COMPOUNDS TO PROMOTE NORMAL PROCESSING OF APP

CROSS-REFERENCE TO RELATED APPLICATIONS

This application is a 371 National Phase of PCT/US2012/049223, filed on Aug. 1, 2012, which claims benefit of and priority to U.S. Ser. No. 61/514,381, filed on Aug. 2, 2011, which is incorporated herein by reference in its entirety for all purposes.

STATEMENT OF GOVERNMENTAL SUPPORT

This work was supported in part by Grant No R01 AG034427 from the National Institutes of Health, National Institute ort Aging. The Government has certain rights in this invention.

BACKGROUND

Alzheimer's disease (AD) is a progressive neurodegenerative disorder that is characterized by rapid cognitive and functional decline in patients diagnosed with the disease. In the early stages of the disease the patients generally suffer from mild cognitive impairment (MCI) that converts over time to full blown AD. The disease broadly falls into two categories: a) late onset AD, which occurs generally at 65 years or older and is correlated to numerous risk factors including presence of an APOE ε4 allele; and b) early onset AD, which develops early on between 30 and 60 years of age and is generally associated with familial Alzheimer's disease (FAD) mutations in the amyloid precursor protein (APP) gene or in the presenilin gene. In both types of disease, the pathology is the same but the abnormalities tend to be more severe and widespread in cases beginning at an earlier age.

The disease is characterized by at least two types of lesions in the brain, senile plaques composed of the Aβ peptide (and other components, typically at lower concentrations than the Aβ peptide) and neurofibrillary tangles composed primarily of intracellular deposits of microtubule associated tau protein (especially hyperphosphorylated tau). Measurement of the levels of Aβ peptide and Tau/phosphorylated Tau in cerebrospinal fluid (CSF) along with imaging analysis and cognitive/functional tests are used clinically to determine progression of the disease and conversion to full-blown AD.

Alzheimer's disease (AD) has been viewed largely as a disease of toxicity, mediated by the collection of a small peptide (the Aβ peptide) that damages brain cells by physical and chemical properties, such as the binding of damaging metals, reactive oxygen species production, and direct damage to cell membranes. While such effects of Aβ have been clearly demonstrated, they do not offer a physiological role for the peptide.

Recent results from several different laboratories suggest Aβ has physiological signaling properties (e.g., via interaction with APP itself, the insulin-receptor, and other receptors), and our results suggest that AD may result from an imbalance between two normal processes: memory formation and normal forgetting. Our studies show that APP has all of the characteristics of a dependence-receptor, i.e., a receptor that mediates cell-death in the presence of an anti-trophin (in this case, Aβ), but supports cell survival in the presence of a trophic-factor (such as laminin).

Several significant changes have occurred in the AD landscape recently. Two therapies that showed marked reduction of β-amyloid levels in AD patients with limited to no cognitive improvement (Mangialasche, et al., (2010) *Lancet Neurol.* 9, 702-716). This was unexpected by much of the research community, as AD has been largely viewed as a disease of chemical and physical toxicity of β-amyloid (e.g., generation of reactive oxygen species, metal binding, etc.). However, recent results from multiple laboratories suggest a completely different view of AD as an imbalance in physiological signal transduction.

For example Lu et al., (2000) *Nat. Med.*, 6: 397-404 and Galvan et al., (2006) *Proc. Natl. Acad. Sci. USA*, 103:7130-7135 have shown a role of APP in mechanisms of signal transduction leading to neuronal cell death. These results, coupled with others, argue that Alzheimer's disease results from an imbalance between two normal processes: memory formation and normal forgetting. The data show that the Aβ peptide can play a role in modulating, processing and signaling through binding to the amyloid precursor protein (APP), and thus play a central role in the pathogenesis of Alzheimer's disease through signaling rather than chemical and physical effects.

APP695 can be cleaved by caspases at an intracellular site (Asp664), leading to the release of a small C31 peptide and an APPneo (APP664) fragment, and both products are potentially proapoptotic (Galvan et al., supra). Immunohistochemical analysis of AD brain demonstrates that this cytoplasmic cleavage occurs 4-fold more in AD brain than normal, and the products are found around plaques and tangles in key brain areas affected by the disease (Bredesen et al., (2006) *Nature* 443: 796-802). Through a single genetic mutation in the amyloid precursor protein (APP the AD phenotype was reversed in a transgenic mouse model by producing a mutation of aspartic acid residue 664 to alanine of APP695 leading to the complete blockage of the C-terminal cleavage in vivo. In addition, these transgenic mice demonstrate normal synaptic function and normal memory. Furthermore, it has been shown in cell culture that this C-terminal cleavage requires Aβ-facilitated APP multimerization. The striking result of this research—that blockage of the D664 cleavage of APP leads to abrogation of the characteristic pathophysiological abnormalities and behavioral symptoms associated with Alzheimer's disease—argues recognition of this mechanism can be of fundamental importance in developing novel therapeutic agents for treatment for AD.

SUMMARY

In certain embodiments, methods are provided that use tropinol esters and related esters (as described herein) in the modulation, and in particular in the reduction of amyloidogenic pathologies (e.g., Alzheimer's disease, age-related macular degeneration (AMD), Cerebrovascular dementia, Parkinson's disease, and the like). In particular, in certain embodiments, tropinol esters (and related esters) described herein are used to mitigate in a mammal one or more symptoms associated with a disease characterized by amyloid deposits in the brain, or delaying or preventing the onset of said symptoms, are provided. In certain embodiments, methods of reducing the risk, lessening the severity, or delaying the progression or onset of a disease characterized by beta-amyloid deposits in the brain of a mammal are also provided. In addition, methods of promoting the processing of amyloid precursor protein (APP) by the non-amyloidogenic pathway (e.g., increasing sAPPα and/or the sAPPα/

Aβ42 ratio) in a mammal are provided. In certain embodiments, methods of directly or indirectly inhibiting the C-terminal cleavage of APP resulting in the formation of APP-C31 peptide and APPneo (APP664) in a mammal are provided.

Generally, the methods involve administration of one or more of the tropinol esters and/or related compounds described herein in an amount sufficient to produce the desired result.

In certain embodiments methods of mitigating in a mammal one or more symptoms associated with a disease characterized by amyloid deposits in the brain, or delaying or preventing the onset of the symptoms are provided where the methods comprise administering, or causing to be administered, to the mammal one or more compounds according to a Formula I, and/or Formula II, and/or Formula III described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof, where the administering is in an amount sufficient to mitigate one or of said more symptoms.

In certain embodiments methods of reducing the risk, and/or lessening the severity, and/or delaying the progression or onset of a disease characterized by beta-amyloid deposits in the brain of a mammal are provided where the methods comprise administering, or causing to be administered, to the mammal one or more compounds according to a Formula I, and/or Formula II, and/or Formula III described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof, where the administering is in an amount sufficient to reduce the risk, and/or lessen the severity, and/or delay the progression or onset of the disease. In certain embodiments the disease is a disease selected from the group consisting of MCI, Alzheimer's disease, age-related macular degeneration (AMD), Cerebrovascular dementia, Parkinson's disease, Huntington's disease, and Cerebral amyloid angiopathy. In certain embodiments the disease is MCI. In certain embodiments, the disease is Alzheimer's disease. In certain embodiments, the disease is age-related macular degeneration (AMD). In certain embodiments, the disease is cerebrovascular dementia. In certain embodiments, the disease is Parkinson's disease. In certain embodiments, the disease is Huntington's disease. In certain embodiments, the disease is Cerebral amyloid angiopathy.

In certain embodiments methods of preventing or delaying the onset of a pre-Alzheimer's condition and/or cognitive dysfunction, and/or ameliorating one or more symptoms of a pre-Alzheimer's condition and/or cognitive dysfunction, and/or preventing or delaying the progression of a pre-Alzheimer's condition or cognitive dysfunction to Alzheimer's disease in a mammal are provided where the methods comprise administering, or causing to be administered, to the mammal one or more compounds according to a Formula I, and/or Formula II, and/or Formula III described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof, where the administering is in an amount sufficient to promote the processing of amyloid precursor protein (APP) by the non-amyloidogenic pathway.

In certain embodiments methods of promoting the processing of amyloid precursor protein (APP) by the non-amyloidogenic pathway, e.g., as characterized by increasing sAPPα and/or the sAPPα/Aβ42 ratio in a mammal, are provided where the methods comprise administering, or causing to be administered, to the mammal one or more compounds according to a Formula I, and/or Formula II, and/or Formula III described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof, where the administering is in an amount sufficient to promote the processing of amyloid precursor protein (APP) by the non-amyloidogenic pathway.

In certain embodiments methods method of inhibiting the C-terminal cleavage of APP (e.g., a cleavage that results resulting in the formation of APP-C31 peptide and APPneo (APP664)) in a mammal are provided where the methods comprise administering, or causing to be administered, to the mammal one or more compounds according to a Formula I, and/or Formula II, and/or Formula III described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof, where the administering is in an amount sufficient to reduce or stop the C-terminal cleavage of APP.

In certain embodiments in any of the foregoing methods in Formula I, and/or Formula II, and/or Formula III:

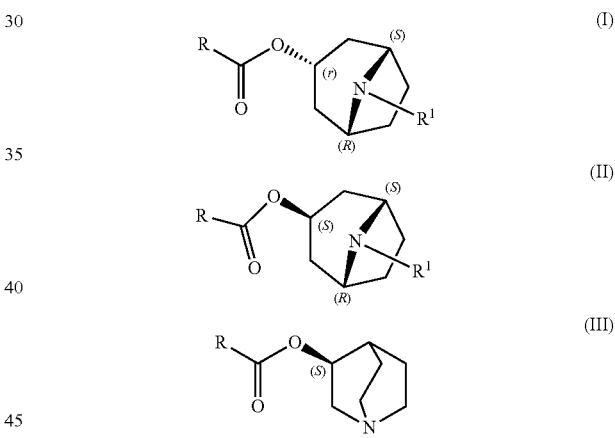

R is selected from the group consisting of H, substituted alkyl, unsubstituted alkyl, cycloalkyl, substituted cycloalkyl, aryl, substituted aryl, heteroaryl, benzofuran, isobenzofuran, indole, isoindole, indazole benzothiophene, benzo[c]thiophene, benzimidazole purine, benzoxazole, benzisoxazole, benzothiazole, naphathalene, quinolone, qinoxaline, isoquinoline, quinazoline, cinnoline, and acridine; $R^1$ is selected from the group consisting of substituted alkyl, substituted alkyl, cycloalkyl, substituted cycloalkyl, alkylether, phenyl, and substituted phenyl; and R is not any one or more or not any of:

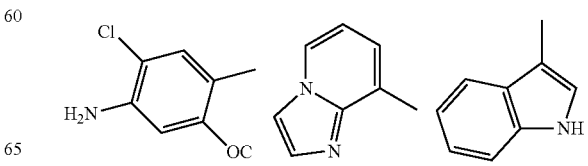

In certain embodiments, the compound is a compound according to any one of formulas IV, V, VI, VII, VIII, IX, X, XI, XII, XIII, XIV, XV, XVI, XVII, XVIII, XIX, XX, XXI, and XXII as described herein or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In certain embodiments the compound any one of compound 4, compound 5, compound 7, compound 9, compound 1, compound 11, compound 12, compound 13, compound 14, and compound and 2 as described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In various embodiments of these methods, the mammal is a human. In certain embodiments the mammal is (e.g., a human) diagnosed as having or as at risk for a pre-Alzheimer's condition and/or cognitive dysfunction. In certain embodiments the mammal is (e.g., a human) diagnosed as at risk for or as having mild cognitive impairment (MCI). In certain embodiments the administration of the compound delays or prevents the progression of a pre-Alzheimer's condition and/or cognitive dysfunction to MCI or to Alzheimer's disease and/or the progression of MCI to Alzheimer's disease. In certain embodiments the disease in the foregoing methods is Alzheimer's disease. In certain embodiments the mammal is diagnosed as having Alzheimer's disease. In certain embodiments the mammal (e.g., human) is at risk of developing Alzheimer's disease. In certain embodiments the mammal (e.g., human) has a familial risk for having Alzheimer's disease. In certain embodiments the mammal (e.g., human) has a familial Alzheimer's disease (FAD) mutation. In certain embodiments the mammal (e.g., human) has the APOE ε4 allele. In certain embodiments the mammal (e.g., human) is free of and does not have genetic risk factors of for a neurological disorder not associated with or characterized by the formation of beta-amyloid plaques. In certain embodiments the mammal (e.g., human) is not diagnosed as having or at risk schizophrenia or other neuropsychiatric disorders. In certain embodiments the mammal (e.g., human) does not have a neurological disease or disorder other than Alzheimer's disease. In certain embodiments the mammal (e.g., human) is not diagnosed as having or at risk for a neurological disease or disorder other than Alzheimer's disease. In certain embodiments in the foregoing methods, the mitigation comprises a reduction in the CSF of levels of one or more components selected from the group consisting of Tau, phospho-Tau (pTau), APPneo, soluble Aβ40 and soluble Aβ 42. In certain embodiments the mitigation comprises a reduction of the plaque load in the brain of the mammal. In certain embodiments the mitigation comprises a reduction in the rate of plaque formation in the brain of the mammal. In certain embodiments the mitigation comprises an improvement in the cognitive abilities of the mammal. In certain embodiments the mammal is a human and the mitigation comprises a perceived improvement in quality of life by the human. In certain embodiments the compound is administered orally. In certain embodiments administering is over a period of at least three weeks. In certain embodiments the administering is over a period of at least 6 months. In certain embodiments the compound is formulated for administration via a route selected from the group consisting of isophoretic delivery, transdermal delivery, aerosol administration, administration via inhalation, oral administration, intravenous administration, and rectal administration. In certain embodiments the compound is administered via a route selected from the group consisting of isophoretic delivery, transdermal delivery, aerosol administration, administration via inhalation, oral administration, intravenous administration, and rectal administration.

In various embodiments a compound for use in 1) mitigating in a mammal one or more symptoms associated with a disease characterized by amyloid deposits in the brain, and/or in delaying or preventing the onset of symptoms of such a disease; and/or 2) reducing the risk, lessening the severity, or delaying the progression or onset of a disease characterized by beta-amyloid deposits in the brain of a mammal; and/or 3) preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease in a mammal; and/or 4) promoting the processing of amyloid precursor protein (APP) by the non-amyloidogenic pathway as characterized by increasing sAPPα and/or the sAPPα/Aβ42 ratio in a mammal; and/or 5) the treatment and/or prophylaxis of age-related macular degeneration (AMD) is provided where the compound is a compound according to a Formula I, and/or Formula II, and/or Formula III as described herein, and/or a derivative, an analog, an enantiomer, a mixture of enantiomers, or a mixture of two or more diastereomers thereof, and/or a polymorph thereof. In certain embodiments in any of the compounds of Formula I, and/or Formula II, and/or Formula III:

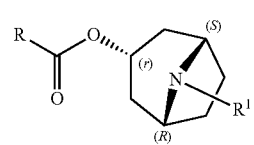

(I)

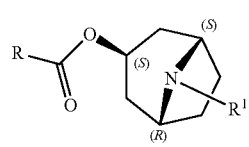

(II)

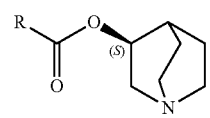

(III)

R is selected from the group consisting of H, substituted alkyl, unsubstituted alkyl, cycloalkyl, substituted cycloalkyl, aryl, substituted aryl, heteroaryl, benzofuran, isobenzofuran, indole, isoindole, indazole benzothiophene, benzo[c]thiophene, benzimidazole purine, benzoxazole, benzisoxazole, benzothiazole, naphathalene, quinolone, qinoxaline, isoquinoline, quinazoline, cinnoline, and acridine; $R^1$ is selected from the group consisting of substituted alkyl, substituted alkyl, cycloalkyl, substituted cycloalkyl, alkylether, phenyl, and substituted phenyl; and R is not any one or more or not any of:

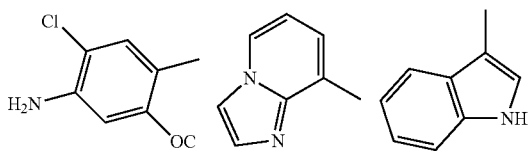
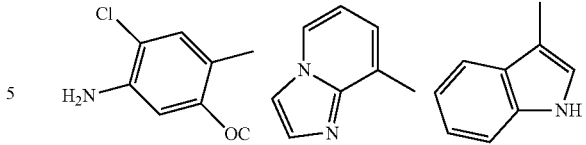

In certain embodiments, the compound is a compound according to any one of formulas IV, V, VI, VII, VIII, IX, X, XI, XII, XIII, XIV, XV, XVI, XVII, XVIII, XIX, XX, XXI, and XXII as described herein or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In certain embodiments the compound any one of compound 4, compound 5, compound 7, compound 9, compound 1, compound 11, compound 12, compound 13, compound 14, and compound and 2 as described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In certain embodiments the compound is present in a composition. In certain embodiments the composition is a pharmaceutical formulation.

In various embodiments, compounds according to Formula I, and/or Formula II, and/or Formula III, as described herein, are provided. In certain embodiments in any of the compounds of Formula I, and/or Formula II, and/or Formula III:

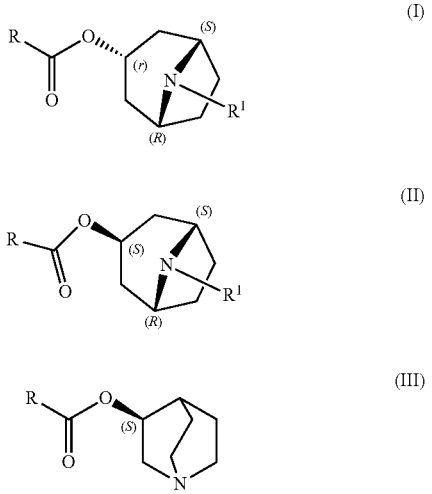

R is selected from the group consisting of H, substituted alkyl, unsubstituted alkyl, cycloalkyl, substituted cycloalkyl, aryl, substituted aryl, heteroaryl, benzofuran, isobenzofuran, indole, isoindole, indazole benzothiophene, benzo[c]thiophene, benzimidazole purine, benzoxazole, benzisoxazole, benzothiazole, naphathalene, quinolone, qinoxaline, isoquinoline, quinazoline, cinnoline, and acridine; $R^1$ is selected from the group consisting of substituted alkyl, substituted alkyl, cycloalkyl, substituted cycloalkyl, alkylether, phenyl, and substituted phenyl; and R is not any one or more or not any of:

In certain embodiments, the compound is a compound according to any one of formulas IV, V, VI, VII, VIII, IX, X, XI, XII, XIII, XIV, XV, XVI, XVII, XVIII, XIX, XX, XXI, and XXII as described herein or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In certain embodiments the compound any one of compound 4, compound 5, compound 7, compound 9, compound 1, compound 11, compound 12, compound 13, compound 14, and compound and 2 as described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof.

Also provided are pharmaceutical formulations comprising the compounds according to Formula I, and/or Formula II, and/or Formula III, as described herein, or a derivative, an analog, an enantiomer, a mixture of enantiomers, or a mixture of two or more diastereomers thereof, or a polymorph thereof are provided. In certain embodiments, the compound is a compound according to any one of formulas IV, V, VI, VII, VIII, IX, X, XI, XII, XIII, XIV, XV, XVI, XVII, XVIII, XIX, XX, XXI, and XXII as described herein or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In certain embodiments the compound any one of compound 4, compound 5, compound 7, compound 9, compound 1, compound 11, compound 12, compound 13, compound 14, and compound and 2 as described herein, or a derivative, an analog, an enantiomer, a mixture of enantiomers, or a mixture of two or more diastereomers thereof, or a polymorph thereof; and/or a pharmaceutically acceptable salt, ester, amide, solvate, hydrate, or prodrug thereof. In certain embodiments the formulation is formulated for administration via a route selected from the group consisting of oral administration, nasal administration, administration via inhalation, oral administration, rectal administration, intraperitoneal injection, intravascular injection, subcutaneous injection, transcutaneous administration, and intramuscular injection. In certain embodiments the formulation is a unit dosage formulation. In certain embodiments the formulation is sterile.

In various embodiments methods for the treatment or prophylaxis of age related macular degeneration (AMD) in a mammal are provided where the method comprises administering to a mammal in need thereof a composition comprising a compound according to Formula I, Formula II, or Formula III, as described herein, or a derivative, an analog, an enantiomer, a mixture of enantiomers, or a mixture of two or more diastereomers thereof; or a polymorph thereof in an amount sufficient to ameliorate one or more symptoms of AMD and/or to slow the progression of AMD, and/or to reverse the effects of AMD. In certain embodiments the administration is intraocular administration. In certain embodiments the intraocular administration is achieved via an injection. In certain embodiments the administration is oral administration. In various embodiments the mammal is a human (e.g., a human diagnosed as having or as at risk for AMD).

In certain embodiments of any of the methods, uses, or compound described herein, the active agents described herein (e.g., tropinol esters and related esters, analogs, derivatives and prodrugs thereof described herein) expressly exclude tropisetron, tropisetron analogs and the various compounds described in U.S. patent application Ser. No. 13/213,960 (U.S. Patent Publication No: US-2012-0071468-A1), and in PCT Application No: PCT/US2011/048472 (PCT Publication No: WO 2012/024616), and in U.S. Pat. Nos. 4,789,673 and 5,998,429. In certain embodiments the active agents, methods of treatment and/or prophylaxis, and uses thereof described herein expressly exclude any one of the compounds disclosed in the foregoing applications. In certain embodiments the active agents, methods of treatment and/or prophylaxis, and uses thereof described herein expressly exclude any one or more of the compounds disclosed in the foregoing applications. In certain embodiments the active agents, methods of treatment and/or prophylaxis, and uses thereof described herein expressly exclude all of the compounds disclosed in the foregoing applications.

Definitions

Generally, reference to a certain element such as hydrogen or H is meant to include all isotopes of that element. For example, if an R group is defined to include hydrogen or H, it also includes deuterium and tritium. Accordingly, isotopically labeled compounds are within the scope of this invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (e.g., F, Cl, Br, and I); hydroxyls; alkoxy, alkenoxy, alkynoxy, aryloxy, arylalkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (e.g., CN), and the like.

The term "alkyl" refers to and covers any and all groups that are known as normal alkyl, branched-chain alkyl, cycloalkyl and also cycloalkyl-alkyl.

The term "$C_{1-6}$ alkyl group" refers to a straight chain or branched chain alkyl group having 1 to 6 carbon atoms, and may be exemplified by a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, and an n-hexyl group.

Aryl groups are cyclic aromatic hydrocarbons that do not contain heteroatoms. Aryl groups include monocyclic, bicyclic and polycyclic ring systems. Thus, aryl groups include, but are not limited to, phenyl, a zulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

The term "heteroaryl group" refers to a monocyclic or condensed-ring aromatic heterocyclic group containing one or more hetero-atoms selected from O, S and N. If the aromatic heterocyclic group has a condensed ring, it can include a partially hydrogenated monocyclic group. Examples of such a heteroaryl group include a pyrazolyl group, a thiazolyl group, an isothiazolyl group, a thiadiazolyl group, an imidazolyl group, a furyl group, a thienyl group, an oxazolyl group, an isoxazolyl group, a pyrrolyl group, an imidazolyl group, a (1,2,3)- and (1,2,4)-triazolyl group, a tetrazolyl group, a pyranyl group, a pyridyl group, a pyrimidinyl group, a pyrazinyl group, a pyridazinyl group, a quinolyl group, an isoquinolyl group, a benzofuranyl group, an isobenzofuranyl group, an indolyl group, an isoindolyl group, an indazolyl group, a benzoimidazolyl group, a benzotriazolyl group, a benzoxazolyl group, a benzothiazolyl group, a benzo[b]thiophenyl group, a thieno[2,3-b]thiophenyl group, a (1,2)- and (1,3)-benzoxathiol group, a chromenyl group, a 2-oxochromenyl group, a benzothiadiazolyl group, a quinolizinyl group, a phthalazinyl group, a naphthyridinyl group, a quinoxalinyl group, a quinazolinyl group, a cinnolinyl group, and a carbazolyl group.

A "derivative" of a compound means a chemically modified compound wherein the chemical modification takes place at one or more functional groups of the compound. The derivative however, is expected to retain, or enhance, the pharmacological activity of the compound from which it is derived and/or to reduce undesired side effects of the compound when administered to a mammal.

As used herein, the phrase "a subject in need thereof" refers to a subject, as described infra, that suffers or is at a risk of suffering (e.g., pre-disposed such as genetically pre-disposed) from the diseases or conditions listed herein.

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

An "effective amount" refers to an amount effective, at dosages and for periods of time necessary, to achieve the desired therapeutic or prophylactic result. A "therapeutically effective amount" of a multi-component formulation, optionally in combination with one or more pharmaceuticals, may vary according to factors such as the disease state, age, sex, and weight of the individual, the pharmaceutical (and dose thereof) when used in combination with pharmaceutical, and the ability of the treatment to elicit a desired response in the individual. A therapeutically effective amount is also one in which any toxic or detrimental effects of a treatment are substantially absent or are outweighed by the therapeutically beneficial effects. The term "therapeutically effective amount" refers to an amount of an active agent or composition comprising the same that is effective to "treat" a disease or disorder in a mammal (e.g., a patient). In one embodiment, a therapeutically effective amount is an amount sufficient to improve at least one symptom associated with a neurological disorder, improve neurological function, improve cognition, or one or more markers of a neurological disease, or to enhance the efficacy of one or more pharmaceuticals administered for the treatment or prophylaxis of a neurodegenerative pathology. In certain embodiments, an effective amount is an amount sufficient alone, or in combination with a pharmaceutical agent to prevent advancement or the disease, delay progression, or to cause regression of a disease, or which is capable of reducing symptoms caused by the disease, A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

The terms "treatment," "treating," or "treat" as used herein, refer to actions that produce a desirable effect on the symptoms or pathology of a disease or condition, particularly those that can be effected utilizing the multi-component formulation(s) described herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrases "improve at least one symptom" or "improve one or more symptoms" or equivalents thereof, refer to the reduction, elimination, or prevention of one or more symptoms of pathology or disease. Illustrative symptoms of pathologies treated, ameliorated, or prevented by the compositions described herein (e.g., tropinol esters and related esters) include, but are not limited to, reduction, elimination, or prevention of one or more markers that are characteristic of the pathology or disease (e.g., of total-Tau (tTau), phospho-Tau (pTau), APPneo, soluble Aβ40, pTau/Ap42 ratio and tTau/Ap42 ratio, and/or an increase in the CSF of levels of one or more components selected from the group consisting of Aβ42/Aβ40 ratio, Aβ42/Aβ38 ratio, sAPPα, βAPPα/βAPPβ ratio, βAPPα/Aβ40 ratio, βAPPα/Aβ42 ratio, etc.) and/or reduction, stabilization or reversal of one or more diagnostic criteria (e.g., clinical dementia rating (CDR)). Illustrative measures for improved neurological function include, but are not limited to the use of the mini-mental state examination (MMSE) or Folstein test (a questionnaire test that is used to screen for cognitive impairment), the General Practitioner Assessment of Cognition (GPCOG), a brief screening test for cognitive impairment described by Brodaty et al., (2002) *Geriatrics Society* 50(3): 530-534, and the like.

The phrase "cause to be administered" refers to the actions taken by a medical professional (e.g., a physician), or a person prescribing and/or controlling medical care of a subject, that control and/or determine, and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

BRIEF DESCRIPTION OF THE DRAWINGS

FIG. 1A: Illustrative, but non-limiting non-cyclic species. FIG. 1A: Illustrative, but non-limiting cyclic species.

DETAILED DESCRIPTION

Figure 1A:
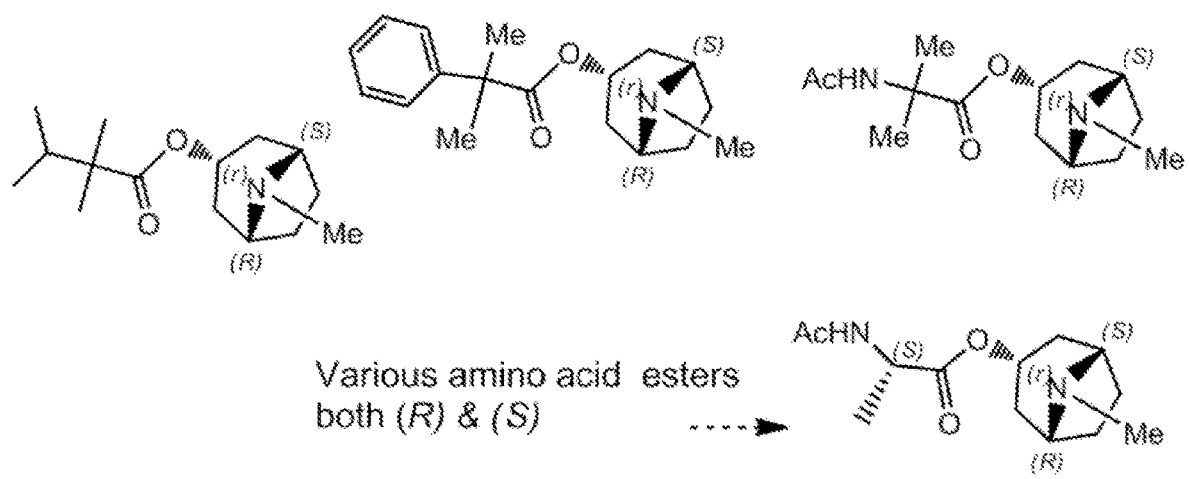
FIGS. 1A and 1B illustrate certain species of Formula X.

The prevailing view of Alzheimer's disease (AD) is that amyloid-beta peptides cause toxicity through chemical and physical mechanisms, such as metal binding, ROS production, and membrane damage. Our data suggest an alternative view of AD as an imbalance in physiological signaling mediated by APP. In this model, Aβ functions physiologically as an anti-trophin, and Aβ binding to APP induces the formation of peptides that mediate neurite retraction and cell death (see, e.g., Lu et al., (2000) *Nat. Med.*, 6: 397-404).

The methods described herein are based, in part, on the surprising discovery that tropinol esters (and related esters) show enhanced transport across the blood brain barrier, and or enhanced bioavailablity (amount, persistence, stability, etc.) and, accordingly enhanced efficacy in promoting processing of amyloid beta (Aβ) precursor protein ("APP") by the nonamyloidogenic ("anti-AD") pathway and/or in reducing or inhibiting processing of APP by the amyloidogenic ("pro-AD") pathway as compared for example to the corresponding amide forms. Without being bound to a particular theory, this is believed to result in reduced production of Aβ, that may be deposited in amyloid plaques in the brain and the other pro-AD fragments known to result in neurotoxicity.

Accordingly, in various embodiments, the use of tropinol esters and related esters (as described herein) is contemplated in the modulation, and in particular in the reduction of amyloidogenic pathologies (e.g., Alzheimer's disease, age-related macular degeneration (AMD), Cerebrovascular dementia, Parkinson's disease, and the like). In certain embodiments, the tropinol esters (and related esters) described herein are used to prevent or delay the onset of a pre-Alzheimer's condition and/or cognitive dysfunction, and/or to ameliorate one or more symptoms of a pre-Alzheimer's condition and/or cognitive dysfunction, and/or to prevent or delay the progression of a pre-Alzheimer's condition or cognitive dysfunction to Alzheimer's disease. In certain embodiments, the tropinol esters (and related esters) described herein are used in a method of mitigating in a mammal one or more symptoms associated with a disease characterized by amyloid deposits in the brain, or delaying or preventing the onset of said symptoms. In certain embodiments, methods of reducing the risk, lessening the severity, or delaying the progression or onset of a disease characterized by beta-amyloid deposits in the brain of a mammal are also provided. In addition, methods of promoting the processing of amyloid precursor protein (APP) by the non-amyloidogenic pathway in a mammal are provided. In certain embodiments, methods of directly or indirectly inhibiting the C-terminal cleavage of APP resulting in the formation of APP-C31 peptide and APPneo ($APP_{664}$) in a mammal are provided.

Typically each of these methods involve administering one or more tropinol esters (and/or related compounds) described herein, in an amount sufficient to produce the desired activity (e.g., mitigating one or more symptoms associated with a disease characterized by amyloid deposits in the brain, or delaying or preventing the onset of said symptoms, and/or reducing the risk, lessening the severity, or delaying the progression or onset of a disease characterized by beta-amyloid deposits in the brain of a mammal, and/or promoting the processing of amyloid precursor protein (APP) by the non-amyloidogenic pathway).

While the methods described herein are detailed primarily in the context of mild cognitive impairment (MCI) and Alzheimer's disease (AD) it is believed they can apply equally to other pathologies characterized by amyloidosis. Illustrative, but non-limiting list of conditions characterized by amyloid plaque formation are shown in Table

TABLE 1

Illustrative, but non-limiting pathologies characterized by amyloid formation/deposition.

| Disease | Characteristic Protein | Abbreviation |
|---|---|---|
| Alzheimer's disease | Beta amyloid | Aβ |
| Diabetes mellitus type 2 | IAPP (Amylin) | AIAPP |
| Parkinson's disease | Alpha-synuclein | |
| Transmissible spongiform encephalopathy e.g. Bovine spongiform encephalopathy | Prion | APrP |
| Huntington's Disease | Huntingtin | |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |
| Prolactinomas | Prolactin | APro |
| Familial amyloid polyneuropathy | Transthyretin | ATTR |
| Hereditary non-neuropathic systemic amyloidosis | Lysozyme | ALys |
| Dialysis related amyloidosis | Beta 2 microglobulin | Aβ2M |
| Finnish amyloidosis. | Gelsolin | AGel |
| Lattice corneal dystrophy | Keratoepithelin | AKer |
| Cerebral amyloid angiopathy | Beta amyloid[15] | Aβ |
| Cerebral amyloid angiopathy (Icelandic type) | Cystatin | ACys |
| systemic AL amyloidosis | Immunoglobulin light chain AL[14] | AL |
| Sporadic Inclusion Body Myositis | S-IBM | none |
| Age-related macular degeneration (AMD) | | |
| Cerebrovascular dementia | | |

Subjects Who Can Benefit from the Present Methods

Subjects/patients amenable to treatment using the methods described herein include individuals at risk of disease (e.g., a pathology characterized by amyloid plaque formation) but not showing symptoms, as well as subjects presently showing symptoms. Accordingly, certain subjects include subjects at increased risk for the onset of a pre-Alzheimer's condition and/or cognitive dysfunction (e.g., MCI) and/or subjects diagnosed as having a pre-Alzheimer's condition and/or cognitive dysfunction (e.g., MCI).

Accordingly, in various embodiments, therapeutic and/or prophylactic methods are provided that utilize the active agent(s) (e.g., tropinol esters and related esters described herein, and analogues, derivatives, or prodrugs thereof) are provided. Typically the methods involve administering one or more active agent(s) (e.g., tropinol esters) to a subject (e.g., to a human in need thereof) in an amount sufficient to realize the desired therapeutic or prophylactic result.

Prophylaxis

In certain embodiments, active agent(s) (e.g., tropinol esters and related esters, analogues, derivatives, or prodrugs thereof) are utilized in various prophylactic contexts. Thus, for example, ion certain embodiments, the active agent(s) (e.g., tropinol esters) can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process(es) (abbreviated as AD-P, see, e.g., Sperling et al., (2011) *Alzheimer's & Dementia*, 1-13) at risk for progression to AD dementia to biomarker-positive individuals who are already demonstrating very subtle decline but not yet meeting standardized criteria for MCI (see, e.g., Albert et al., (2011) *Alzheimer's and Dementia*, 1-10 (doi:10.1016/j.jalz.2011.03.008)).

This latter group of individuals might be classified as "not normal, not MCI" but can be designated "pre-symptomatic" or "pre-clinical or "asymptomatic" or "premanifest"). In various embodiments, this continuum of pre-symptomatic AD can also encompass (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al., (2010) *Lancet Neurol.*, 9: 119-128). This biomarker model parallels proposed pathophysiological sequence of (pre-AD/AD), and is relevant to tracking the preclinical (asymptomatic) stages of AD (see, e.g., FIG. 3 in Sperling et al., (2011) *Alzheimer's & Dementia*, 1-13). Biomarkers of brain amyloidosis include, but are not limited to reductions in CSF $A\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al., (2009) *Neurology*, 73: 294-301; Yaffe et al., (2011) *JAMA* 305: 261-266).

In certain embodiments, the subjects suitable for the prophylactic methods contemplated herein include, but are not limited to subject characterized as having asymptomatic cerebral amyloidosis. In various embodiments, these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomatology.

It is noted that currently available CSF and PET imaging biomarkers of Aβ primarily provide evidence of amyloid accumulation and deposition of fibrillar forms of amyloid. Data suggest that soluble or oligomeric forms of Aβ are likely in equilibrium with plaques, which may serve as reservoirs. In certain embodiments, it is contemplated that there is an identifiable preplaque stage in which only soluble forms of Aβ are present. In certain embodiments, it is contemplated that oligomeric forms of amyloid may be critical in the pathological cascade, and provide useful markers. In addition, early synaptic changes may be present before evidence of amyloid accumulation.

In certain embodiments, the subjects suitable for the prophylactic methods contemplated herein include, but are not limited to, subjects characterized as amyloid positive with evidence of synaptic dysfunction and/or early neurodegeneration. In various embodiments, these subjects have evidence of amyloid positivity and presence of one or more markers of "downstream" AD-P-related neuronal injury. Illustrative, but non-limiting markers of neuronal injury include, but are not limited to (1) elevated CSF tau or phospho-tau, (2) hypometabolism in an AD-like pattern (e.g., posterior cingulate, precuneus, and/or temporoparietal cortices) on FDG-PET, and (3) cortical thinning/gray matter loss in a specific anatomic distribution (e.g., lateral and medial parietal, posterior cingulate, and lateral temporal cortices) and/or hippocampal atrophy on volumetric MRI. Other markers include, but are not limited to fMRI measures of default network connectivity. In certain embodiments, early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (e.g., in later stages of preclinical (asymptomatic) AD).

In certain embodiments, the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments, criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see, e.g., Hardy (1997) *Trends. Neurosci.,* 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al., (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50 years of age). Usually, however, it is not necessary to begin treatment until a patient reaches at least about 40, 50, 60 or 70 years of age.

In some embodiments, the subject is exhibiting symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al., (2010) *Int. J. Alzheimer's Dis.* 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI. In such instances, the methods can delay or prevent the onset of MCI, and or reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

In various embodiments, the tropinol esters and related esters described herein are contemplated in the treatment and/or prophylaxis of age-related cognitive decline and/or in the treatment and/or prophylaxis of mild cognitive impairment (MCI). Mile cognitive impairment, also known as incipient dementia, or isolated memory impairment) is a diagnosis given to individuals who have cognitive impairments beyond that expected for their age and education, but that typically do not interfere significantly with their daily activities (see, e.g., Petersen et al., (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al., (2004) *Arch. Neurol.* 61(1): 59-66; and on the internet at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al., (2006) *Arch. Neurol.,* 63(5): 665-72).

The diagnosis of MCI typically involves a comprehensive clinical assessment including clinical observation, neuroimaging, blood tests and neuropsychological testing. In certain embodiments, diagnostic criteria for MCI include, but are not limited to those described by Albert et al., (2011) *Alzheimer's & Dementia.* 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments, clinical evaluation/diagnosis of MCI involves: (1) Concern reflecting a change in cognition reported by patient or informant or clinician (e.g., historical or observed evidence of decline over time); (2) Objective evidence of Impairment in one or more cognitive domains, typically including memory (e.g., formal or bedside testing to establish level of cognitive function in multiple domains); (3) Preservation of independence in functional abilities; (4) Not demented; and in certain embodiments, (5) An etiology of MCI consistent with AD pathophysiological processes. Typically vascular, traumatic, medical causes of cognitive decline are ruled out where possible. In certain embodiments, evidence of longitudinal decline in cognition is identified, when feasible. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (e.g., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (e.g., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (e.g., mutation in APP, PS1, PS2), then the development of MCI is most likely the precursor to AD dementia. The large majority of these cases develop early onset AD (e.g., onset below 65 years of age).

In addition, there are genetic influences on the development of late onset AD dementia. For example, the presence of one or two ε4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ε4 positive, is more likely to progress to AD dementia within a few years than an individual without this genetic characteristic. It is believed that additional genes play an important, but smaller role than APOE and also confer changes in risk for progression to AD dementia (see, e.g., Bertram et al., (2010) Neuron, 21: 270-281).

In certain embodiments, subjects suitable for the prophylactic methods described herein (e.g., administration of the tropinol esters and/or related esters described herein) include, but need not be limited to subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF A$β_{42}$ and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both Aβ, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Ab accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein.

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be is well suited for the methods described herein Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al., (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al., (2008) *Brain* 131 (Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments, MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 2.

TABLE 2

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Memory | No memory loss or slight inconsistent forgetfulness | Consistent slight forgetfulness; partial recollection of events "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home Appears well enough to be taken to functions outside a family home | Appears too ill to be taken to functions outside a family home. |

TABLE 2-continued

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments, administration of one or more agents described herein (e.g., tropinol esters and related esters described herein, analogues, derivatives, or prodrugs thereof) is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, el al., (2004) *Arch Neurol* 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemory cognitive measures included in the battery. Tests of learning, attention, perceptual speed, category fluency, and executive function may be impaired in patients with MCI, but these are far less prominent than the memory deficit.

Alzheimer's Disease (AD).

In certain embodiments, the active agent(s) (e.g., tropinol esters and related esters described herein, analogues, derivatives, or prodrugs thereof) and/or formulations thereof are contemplated for the treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments, subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al., (1984) *Neurology* 34(7): 939-944. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al., (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al., (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al., supra). Any score greater than or equal to 25 points (out of 30) is effectively normal (intact). Below this, scores can indicate severe ($\leq 9$ points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 3.

TABLE 3

Illustrative stages of Alzheimer's disease

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.

Moderately severe cognitive decline (Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.

Severe cognitive decline (Moderately severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).
Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.
Tend to wander and become lost.

TABLE 3-continued

Illustrative stages of Alzheimer's disease

Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up. Reflexes become abnormal and muscles grow rigid. Swallowing is impaired.

In various embodiments, administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments, subjects amenable to the present methods generally are free of a neurological disease or disorder other than Alzheimer's disease. For example, in certain embodiments, the subject does not have and is not at risk of developing a neurological disease or disorder such as Huntington's Disease, and/or Parkinson's disease, and/or schizophrenia, and/or psychosis.

In various embodiments, the effectiveness of treatment can be determined by comparing a baseline measure of a parameter of disease before administration of the active agent(s) (e.g., tropinol esters and related esters described herein) is commenced to the same parameter one or more time points after the formulation has been administered. One illustrative parameter that can be measured is a biomarker (e.g., a peptide oligomer) of APP processing. Such biomarkers include, but are not limited to increased levels of sAPPα, p3 (Aβ 17-42 or Aβ 17-40), βAPPβ, soluble Aβ40, and/or soluble Aβ42 in the blood, plasma, serum, urine, mucous or cerebrospinal fluid (CSF). Detection of increased levels of sAPPα and/or p3, and decreased levels of βAPPβ and/or APPneo is an indicator that the treatment is effective. Conversely, detection of decreased levels of sAPPα and/or p3, and/or increased levels of βAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MRI.

In various embodiments, administration of the active agent(s) described herein can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

In certain embodiments, the monitoring methods can entail determining a baseline value of a measurable biomarker or parameter (e.g., amyloid plaque load or cognitive abilities) in a subject before administering a dosage of the multi-component formulation and optionally one or more pharmaceuticals, and comparing this biomarker or parameter with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared With a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

In various embodiments, the tissue sample for analysis is typically blood, plasma, serum, urine, mucous or cerebrospinal fluid from the subject.

Tropinol Esters and Related Compounds.

In various embodiments, methods are contemplated that use tropinol (N-Methyl-8-azabicyclo[3.2.1]octan-3-ol) esters and closely related compounds. In certain embodiments, the compounds include compounds according to formulas I, II, or III:

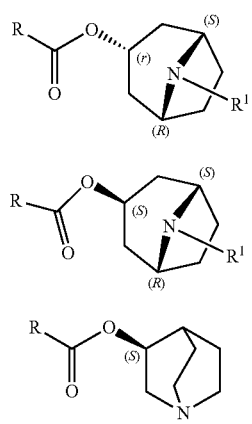

or a derivative, an enantiomer, a mixture of enantiomers, or a mixture of two or more diastereomers thereof; or a pharmaceutically acceptable salt, ester, amide, solvate, hydrate, or prodrug thereof, where $R^1$ is selected from the group consisting of substituted alkyl, unsubstituted alkyl, cycloalkyl, substituted cycloalkyl, alkylether, phenyl, and substituted phenyl, and where R is selected from the group consisting of H, substituted alkyl, unsubstituted alkyl, cycloalkyl, substituted cycloalkyl, aryl, substituted aryl, heteroaryl, benzofuran, isobenzofuran, indole, isoindole, indazole benzothiophene, benzo[c]thiophene, benzimidazole purine, benzoxazole, benzisoxazole, benzothiazole, naphathalene, quinolone, qinoxaline, isoquinoline, quinazoline, cinnoline, and acridine; and R is not

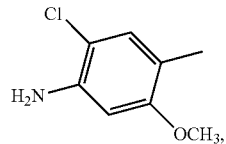

and/or

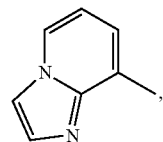

and/or

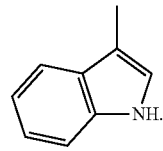

In certain of these embodiments $R^1$ is a $C_1$-$C_6$ alkyl. In certain of these embodiments $R^1$ is $CH_3$. In certain embodiments, R in Formula I, and/or Formula II, and/or Formula III is a compound according to one of Formulas A, B, C, D, E, F, G, or H in U.S. Pat. No. 5,434,161 (and as reproduced in Table 4 below). In certain embodiments, R in Formula I, and/or Formula II, and/or Formula III excludes Formula A, and/or Formula B, and/or Formula C, and/or Formula D, and/or Formula E, and/or Formula F, and/or Formula G, and/or Formula H in U.S. Pat. No. 5,434,161 and as reproduced in Table 4 below)

TABLE 4

Formulas A-H from U.S. Pat. No. 5,434,161.

| Formula | Structure | Substituents |
|---|---|---|
| A | 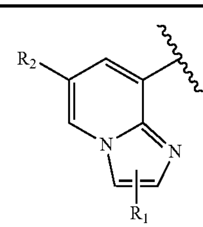 | $R_1$ is H, or C1-6 alkyl, $R_2$ is H, or halogen |
| B | 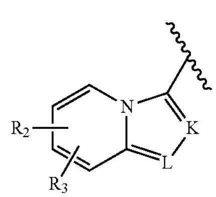 | K is N or $CR_4$, L is N or $CR_5$, $R_2$ & $R_3$ are independently H or halogen, $R_4$ is H, or $C_{1-6}$ alkoxy $R_5$ is H, halogen, $CF_3$, $C_{1-6}$ alkyl, $C_{1-6}$ alkoxy, $C_{1-6}$ alkythio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by |

TABLE 4-continued

Formulas A-H from U.S. Pat. No. 5,434,161.

| Formula | Structure | Substituents |
|---|---|---|
| | | one or two groups selected from $C_{1-6}$ alkyl, $C_{3-8}$ cycloalkyl, and $C_{3-8}$ cycloalkyl $C_{1-4}$ alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups; |
| C | (structure with $R_2$, $R_3$, $M$, $R_5$) | M is N or $CR_4$, $R_2$ & $R_3$ are independently H or halogen, $R_4$ is H or $C_{1-6}$ alkoxy $R_5$ is H, halogen, $CF_3$, $C_{1-6}$ alkyl, $C_{1-6}$ alkoxy, $C_{1-6}$ alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by one or two groups selected from $C_{1-6}$ alkyl, $C_{3-8}$ cycloalkyl, and $C_{3-8}$ cycloalkyl$_{1-4}$ alkyl or disubstituted by $C_4$ or $C_5$ polymethylene, phenyl or phenyl $C_{1-4}$ alkyl group optionally the phenyl ring by one or two of halogen, $C_{1-6}$ alkoxy or $C_{1-6}$ alkyl groups |
| D | (structure with $R_2$, $R_3$, $R_6$, $R_7$) | One of $R_6$ and $R_7$ is $C_{1-6}$ alkyl and the other is $C_{1-6}$ alkyl, phenyl or phenyl $C_{1-4}$ alkyl optionally substituted in either phenyl ring by one or two of $C_{1-6}$ alkyl, $C_{1-6}$ alkoxy, or halogen, or $R_6$ & $R_7$ together are $C_{2-6}$ polymethylene or $C_{2-5}$ polymethylene interrupted by an -O-linkage, $R_2$ & $R_3$ are independently H or halogen |
| E | (structure with $R_2$, $R_3$, $R_4$, $R_5$) | $R_4$ is H or $C_{1-6}$ alkoxy, $R_5$ is H or $C_{1-6}$ alkoxy $R_2$ is H, halogen, $CF_3$, $C_{1-6}$ alkyl, $C_{1-6}$ alkoxy, $C_{1-6}$ alkylthio, C1-6 alkylsulfonyl, $C_{1-6}$ alkylsulfinyl, $C_{1-7}$ acyl, cyano, $C_{1-6}$ alkoxycarbonyl, $C_{1-7}$ acyl-5 amino, hydroxy, nitro, amino, aminocarbonyl, or aminosulfonyl, optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene, phenyl or phenyl $C_{1-4}$ alkyl group optionally substituted in the phenyl ring by one or two of halogen, $C_{1-6}$ alkoxy or $C_{1-6}$ alkyl groups $R_2$ & $R_3$ are independently H or halogen |
| F | (structure with $R_1$, $R_2$) | $R_1$ is H, or $C_{1-6}$ alkyl, $R_2$ is H, or halogen |
| G | (structure) | |

TABLE 4-continued

Formulas A-H from U.S. Pat. No. 5,434,161.

| Formula | Structure | Substituents |
|---------|-----------|--------------|
| H | 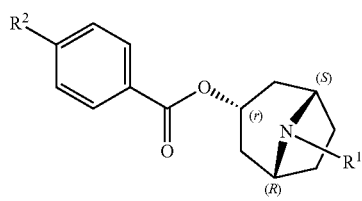 | $R_{15}$ & $R_{16}$ are independently H or —CH=CH—CH=CH—; |

In certain embodiments, the compound is a compound according to Formula IV:

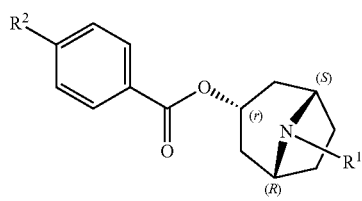

IV where $R^2$ is selected from the group consisting of H, halogen, alkyl, cycloalkyl, trifluoromethyl, N, N-dialkyl, acetyl, O-alkyl, hydroxyl, amino, N-alkyl, O-aryl, O-trifluoromethyl, aryl, heteroaryl, S-alkyl, S-aryl, carboxylate, N-acetyl, alkyl urea, and carbamate. In certain embodiments, $R^2$ is F or Cl. In certain embodiments, $R^1$ is methyl. In certain embodiments, the compound is a compound according to Formula V:

(Compound 5)

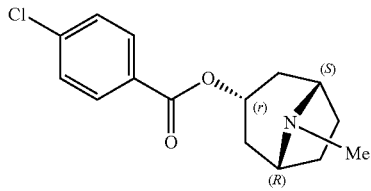

V

In certain embodiments, the compound is a compound according to Formula I where R is selected from the group consisting of naphthalene, quinolone, isoquinoline, cinnoline, quinazoline, quinoxaline, benzofuran, isobenzofuran, isoindole, benzothiophene, benzo[c]thiophene, benzimidazole, purine, benzoxazole, benzisoxazole, and benzthiazole. In certain embodiments, the compound is a compound according to Formula VI:

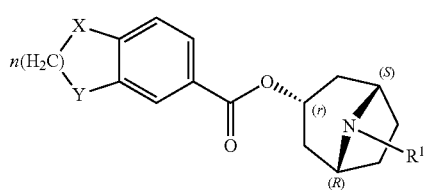

VI

Where in certain embodiments, n is 0 and in certain other embodiments, n is 1, 2, 3, or 4. In certain embodiments, X and Y are independently selected from the group consisting of O, N, and $CH_2$. In certain embodiments, $R^1$ is methyl. In certain embodiments, the compound is a compound according to Formula VII:

(Compound 7)

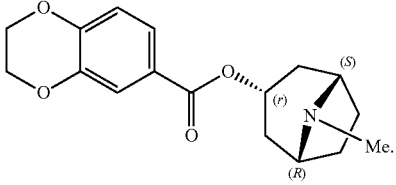

VII

In certain embodiments, the compound is a compound according to Formula VIII:

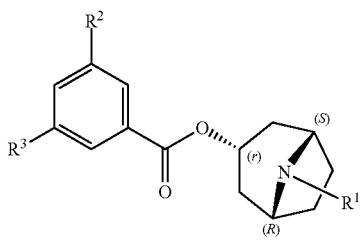

VIII where $R^2$ and $R^3$ are independently selected from the group consisting of H, halogen, alkyl, cycloalkyl, trifluoromethyl, N, N-dialkyl, acetyl, O-alkyl, hydroxyl, amino, N-alkyl, O-aryl, O-trifluoromethyl, aryl, heteroaryl, S-alkyl, S-aryl, carboxylate, N-acetyl, alkyl urea, and carbamate. In certain embodiments, $R^1$ is methyl. In certain embodiments, $R^2$ and $R^3$ are the same, while in other embodiments, $R^2$ and $R^3$ are different. In certain embodiments, $R^2$ and $R^3$ are both Cl or F. In certain embodiments, the compound is a compound according to Formula IX:

(Compound 10)

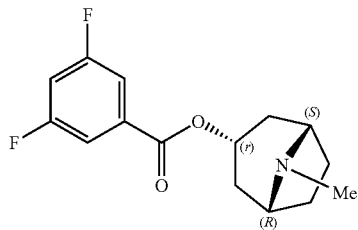

IX

In certain embodiments, the compound is a compound is a compound according to Formula X:

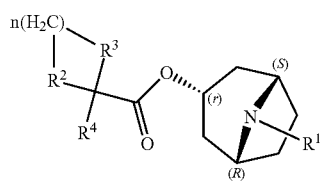

Figure 1B:
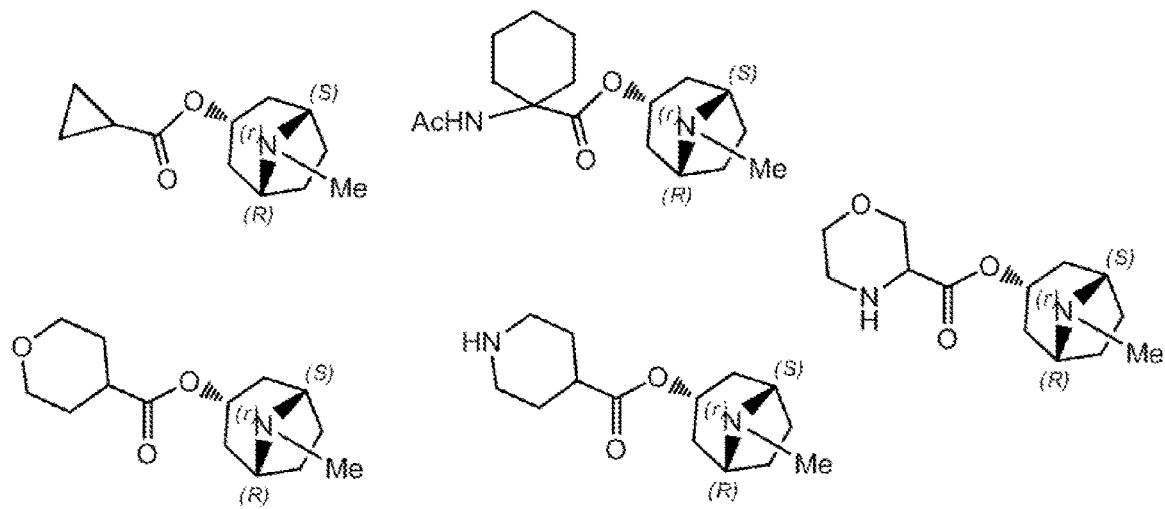

X where n is 0 to 8; $R^4$ is independently selected from the group consisting of H, alklyl, substituted alkyl, aryl, and heteroaryl; and when n=0, $R^2$ and $R^3$ are independently selected from the group consisting of H, alkyl, alkenyl, $OR^5$, $NR^5$, and $SR^5$ where $R^5$ is a protecting group (see, e.g., FIG. 1A); and when n=1-8, $R^2$ taken with $R^3$ form cycloalky or heteroaryl (see, e.g., FIG. 1B). In certain embodiments, $R^5$ is a protecting group selected from the group consisting of acetyl (Ac), amide, a 3 to 20 carbon alkyl group, 9-fluorenylmethyloxycarbonyl (Fmoc), t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-Butyl (tBu), and trifluoroacetyl (TFA). In certain embodiments, (e.g., as illustrated in FIG. 1A) $R^5$ is an acetyl. In certain embodiments, $R^1$ is methyl. In certain embodiments, the compound is a compound according to Formula XI:

(Compound 9)

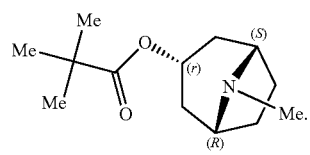

XI

In certain embodiments, the compound is a compound according to Formula I where R is selected from the group consisting of benzene, pyridine, pyrazine, pyrimidine, and pyridazine. In certain embodiments, $R^1$ is methyl. In certain embodiments, the compound is a compound according to Formula XII:

(Compound 13)

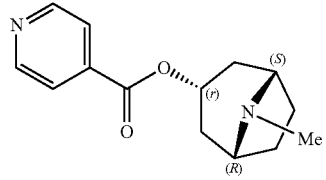

XII

In certain embodiments, the compound is a compound according to Formula I where R is selected from the group consisting of furan, furan, pyrrole, thiophene, imidazole, pyrazole, oxazole, isoxazole, thiazole, thiadizaole, triazole, substituted triazole, tetrazole, and substituted tetrazole. In certain embodiments, $R^1$ is methyl. In certain embodiments, the compound is a compound according to Formula XIII:

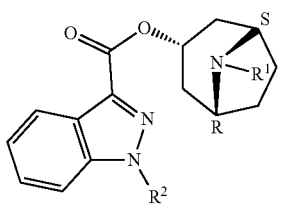

XIII where $R^1$ and $R^2$ are independently selected from the group consisting of H, unsubstituted alkyl, substituted alkyl, cycloalkyl, substituted cycloalkyl, alkylether, phenyl, and substituted phenyl. In certain embodiments, $R^1$ is methyl. In certain embodiments, the compound is a compound according to Formula XIV:

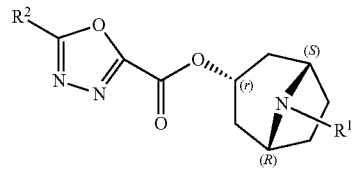

XIV where $R^1$ is selected from the group consisting of substituted alkyl, substituted alkyl, cycloalkyl, substituted cycloalkyl, alkylethers, phenyl, and substituted phenyl, and $R^2$ is selected from the group consisting of alkyl, cycloalkyl, substituted alkyl, aryl, substituted aryl, and heteroaryl. In certain embodiments, $R^1$ is methyl and $R^2$ is H (Compound 11) or $R^1$ is methyl and $R^2$ is $CH_3$ (Compound 14).

In certain embodiments, the compound is a compound according to Formula I, where $R^1$ is methyl. In certain embodiments, the compound is a compound according to Formula XV:

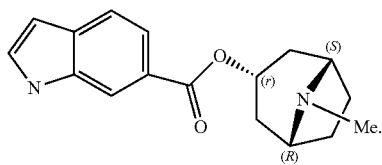
XV

In certain embodiments, the compound is a compound according to Formula XVI:

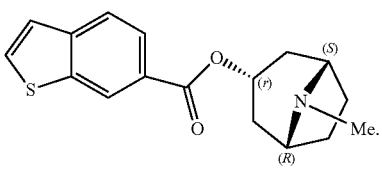
XVI

In certain embodiments, the compound is a compound according to Formula XVII:

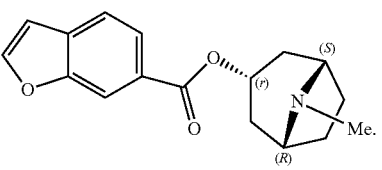
XVII

In certain embodiments, the compound is a compound according to Formula II, where $R^1$ is methyl. In certain embodiments, the compound is a compound according to Formula XVIII:

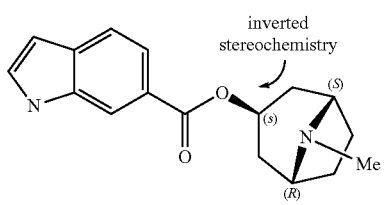
XVIII

In certain embodiments, the compound is a compound according to Formula XIX:

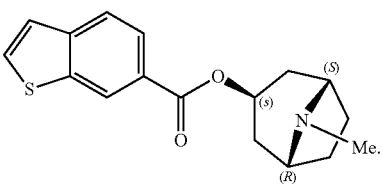
XIX

In certain embodiments, the compound is a compound according to Formula XX:

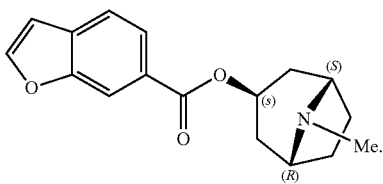
XX

In certain embodiments, the compound is a compound according to Formula XXI:

(Compound 4)

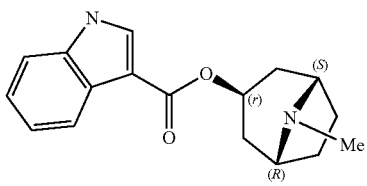
XXI

In certain embodiments, the compound is a compound according to Formula III:

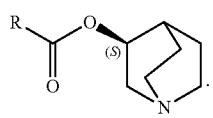
III where R is selected from the group consisting of furan, pyrrole, thiophene, imidazole, pyrazole, oxazole, isoxazole, thiazole, thiadiazole, triazole, substituted triazole, tetrazole, substituted tetrazole, naphthalene, quinolone, isoquinoliine, cinnoline, quinazoline, quinoxaline, bezofuran, isobenzofuran, isoindole, benzothiohene, benzo[c]thiophene, benzimidazole, purine, benzoxazole, benzisoxazole, and benzthiazole. In certain embodiments, R is selected from the group consisting of alkyl, substituted alkyl, cycloalkyl, alkylether, and alkylthioether. In certain embodiments, R is selected from the group consisting of aryl, substituted aryl, heteroaryl, and substituted heteroaryl. In certain embodiments, the compound is a compound according Formula XXI:

(Compound 2)

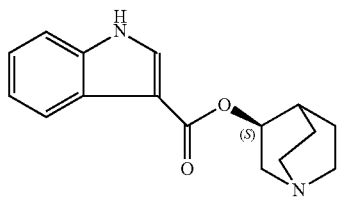
XXII

A non-limiting summary of some preferred species showing APP switching activity and high brain permeability is provided in Table 5.

TABLE 5

Non-limiting examples of 'ester series' analogs with APP switching activity and high brain permeability.

| Compound | Formula |
|---|---|
| XVIII | (indole-6-carboxylate tropinol ester, inverted stereochemistry: (s), (R), (S)) |
| 4 | (indole-3-carboxylate tropinol ester, (r), (R), (S)) |
| 5 | (4-chlorobenzoate tropinol ester, (r), (R), (S)) |
| 7 | (2,3-dihydro-1,4-benzodioxine-6-carboxylate tropinol ester, (r), (R), (S)) |
| 9 | (pivalate / trimethylacetate tropinol ester, (r), (R), (S)) |
| 10 | (3,5-difluorobenzoate tropinol ester, (r), (R), (S)) |
| 11 | (1,3,4-oxadiazole-2-carboxylate tropinol ester, (r), (R), (S)) |
| 12 | (4-fluorobenzoate tropinol ester, (r), (R), (S)) |
| 13 | (isonicotinate tropinol ester, (r), (R), (S)) |
| 14 | (5-methyl-1,3,4-oxadiazole-2-carboxylate tropinol ester, (r), (R), (S)) |
| 2 | (indole-3-carboxylate quinuclidinol ester, (S)) |

The compounds described herein can be synthesized using methods well known to those of skill in the art. For example, synthetic protocols for compounds 2, 4, 5, 7, 9, 10, and 12 are illustrated in the Examples. Using these and other protocols known to those of skill in the art, the compounds described herein are readily available.

Pharmaceutical Formulations.

In certain embodiments, one or more active agents (e.g., the various tropinol esters, related esters, derivatives, prodrugs, etc.) are administered to a mammal in need thereof, e.g., to a mammal at risk for or suffering from a pathology characterized by abnormal processing of amyloid precursor proteins, a mammal at risk for progression of MCI to Alzheimer's disease, and so forth.

The active agent(s) can be administered in the "native" form or, if desired, in the form of salts, esters, amides, prodrugs, derivatives, and the like, provided the salt, ester, amide, prodrug or derivative is suitable pharmacologically, e.g., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, a pharmaceutically acceptable salt can be prepared for any compound described herein having a functionality capable of forming a salt, such as the carboxylic acid or tetrazole functionality of the compounds described herein. A pharmaceutically acceptable salt is any salt which retains the activity of the parent compound and does not impart any deleterious or untoward effect on the subject to which it is administered and in the context in which it is administered.

In various embodiments, pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents described herein (e.g., tropinol esters) are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., amyloidogenic pathologies).

The active agents described herein (e.g., tropinol esters) can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alphastarch, gum arabic, microcrystal line cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., tropinol esters and related esters described herein) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent (s).

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the active agents (e.g., tropinol esters and related esters) described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active agents into preparations that can be used pharmaceutically. Proper formulation is dependent upon the route of administration chosen.

For topical administration the active agents described herein can be formulated as solutions, gels, ointments, creams, suspensions, and the like as are well-known in the art. Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the active agent(s) can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the active agent(s) with pharmaceutically acceptable carriers well known in the art. Such carriers enable the compounds described herein (e.g., tropinol esters) be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the active agent(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the active agent(s) can be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the active agents described herein are administered orally. This is readily accomplished by the use of tablets, caplets, lozenges, liquids, and the like.

In certain embodiments, the active agents described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain embodiments, one or more active agents described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the active agents described herein (e.g., one or more esters described above) are preferably suitable for oral administration. In various embodiments, the active agent(s) in the oral compositions can be either coated or non-coated. The preparation of enteric-coated particles is disclosed for example in U.S. Pat. Nos. 4,786,505 and 4,853,230.

In various embodiments, compositions contemplated herein typically comprise one or more of the various tropinol esters and related compounds described herein in an effective amount to achieve a pharmacological effect or therapeutic improvement without undue adverse side effects. Various effects deemed therapeutic are described above. Illustrative pharmacological effects or therapeutic improvements include, but are not limited to a reduction in the CSF of levels of one or more components selected from the group consisting of Tau, phospho-Tau (pTau), APPneo, soluble Aβ40 and soluble Aβ 42, and/or when a reduction of the plaque load in the brain of the subject, and/or a reduction in the rate of plaque formation in the brain of the subject, and/or an improvement in the cognitive abilities of the subject, and/or a perceived improvement in quality of life by the subject, and/or a significant reduction in clinical dementia rating (CDR) of the subject, and/or a slowing in the rate of increase in clinical dementia rating, and/or when a slowing or stopping in the progression of AD (e.g., when the transition from one stage to another as listed in Table 3 is slowed or stopped).

In various embodiments, the typical daily dose of compound(s) varies and will depend on various factors such as the individual requirements of the patients and the disease to be treated. In general, the daily dose of compounds can be in the range of 1-1,000 mg or 1-800 mg, or 1-600 mg, or 1-500 mg, or 1-400 mg. In one illustrative standard approximate amount of the various tropinol esters and related compounds described above present in the composition can be typically about 1 to 1,000 mg, more preferably about 5 to 500 mg, and most preferably about 10 to 100 mg administered once a day, in certain embodiments, administered twice a day, in certain embodiments, administered 3 times/day, and in certain embodiments, administered 4, or 6, or 6 or 7, or 8 times/day.

The active ingredients of the are preferably formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the various tropinol esters and related compounds described above are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the active agents may be formulated in a single liquid dosage form such as suspension containing all active ingredients or dry suspension to be reconstituted prior to use.

In certain embodiments, the compound(s) are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan;

water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer.

While the compositions and methods are described herein with respect to use in humans, they are also suitable for animal, e.g., veterinary use. Thus certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Combined Treatment Methods and Combined Formulations

In certain instances, one or more of the active agents described above (e.g., tropinol esters, related esters, derivatives thereof, analogs thereof, polymorphs thereof, etc.) are administered in conjunction with one or more additional active agent that are known, or believed, to have utility in the treatment of neurodegenerative diseases including, but not limited to Alzheimer's disease, age-related cognitive impairment, MCI, and the like. The two agents (e.g., tropinol ester or related ester and additional agent) can be administered simultaneously or sequentially. When administered sequentially the two agents are typically administered so that both achieve a physiologically relevant concentration and/or effect over a similar time period (e.g., so that both agents are active at some common time).

In certain instances, one or more of the active agents described above (e.g., tropinol esters, related esters, derivatives thereof, analogs thereof, polymorphs thereof, etc.) are administered before the one or more additional active agents or they are administered after the one or more additional active agents. In certain embodiments one or more of the active agents described above (e.g., tropinol esters, related esters, derivatives thereof, analogs thereof, polymorphs thereof, etc.) are administered simultaneously with one or more additional active agents and in such instances may be formulated as a compound formulation.

Suitable additional active agents include, but are not limited to, Donepezil (e.g., Aricept), Rivastigmine (e.g., EXELON®), Galantamine (e.g., RAZADINE®), Tacrine (e.g., COGNEX®), Memantine (e.g., NAMENDA®), Solanezumab, Bapineuzmab, Alzemed, Flurizan, ELND005, Valproate, Semagacestat, Rosiglitazone, Phenserine, Cernezumab, Dimebon, EGCg, Gammagard, PBT2, PF04360365, NIC5-15, Bryostatin-1, AL-108, Nicotinamide, EHT-0202, BMS708163, NP12, Lithium, ACC001, AN1792, ABT089, NGF, CAD106, AZD3480, SB742457, AD02, Huperzine-A, EVP6124, PRX03140, PUFA, HF02, MEM3454, TTP448, PF-04447943, Ent., GSK933776, MABT5102A, Talsaclidine, UB311, Begacestat, R1450, PF3084014, V950, E2609, MK0752, CTS21166, AZD-3839, LY2886721, CHF5074, anti-inflammatories (e.g., Flurizan (Myriad Genetics), Dapsone, anti-TNF antibodies (e.g., etanercept (Amgen/Pfizer)), and the like), statins (e.g., atorvastatin (LIPITOR®), simvastatin (ZOCOR®, etc.), and the like. In certain embodiments, treatment methods comprising administration of one or more tropinol esters, related esters, derivatives thereof, analogs thereof, polymorphs thereof, and the like described herein in conjunction with any one of the foregoing additional active agents is contemplated. In certain embodiments, treatment methods comprising administration of one or more tropinol esters, related esters, derivatives thereof, analogs thereof, polymorphs thereof, and the like described herein in conjunction with any one or more of the foregoing additional active agents is contemplated.

In certain embodiments, combination formulations comprising one or more tropinol esters, related esters, derivatives thereof, analogs thereof, polymorphs thereof, and the like described herein in combination with any one of the foregoing additional active agents is contemplated. In certain embodiments, combination formulations comprising one or more tropinol esters, related esters, derivatives thereof, analogs thereof, polymorphs thereof, and the like described herein in combination with any one or more of the foregoing additional active agents is contemplated.

In certain embodiments, treatment methods comprising administration of one or more tropinol esters, related esters, derivatives thereof, analogs thereof, polymorphs thereof, and the like described herein in conjunction with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the treatment method comprises administration of tropisetron in conjunction with of one or more tropinol esters, related esters, derivatives thereof, analogs thereof, polymorphs thereof, and the like described herein.

In certain embodiments, combination formulations comprising administration of one or more tropinol esters, related esters, derivatives thereof, analogs thereof, polymorphs thereof, and the like described herein in combination with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213, 960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the combination formulation comprises tropisetron in combination with of one or more tropinol esters, related esters, derivatives thereof, analogs thereof, polymorphs thereof, and the like described herein Assay Systems to Evaluate APP Processing Without being bound to a particular theory, it is believed that, in certain embodiments, tropinol esters and related compounds described herein processing of APP by the nonamyloidogenic pathway and/or reduce or inhibit processing of APP by the amyloidogenic pathway. In the nonamyloidogeic pathway, APP is first cleaved by α-secretase within the Aβ sequence, releasing the APPsα ectodomain ("sAPPα"). In contrast, the amyloidogenic pathway is initiated when β-secretase cleaves APP at the amino terminus of the Aβ, thereby releasing the APPsβ ectodomain ("sAPPβ"). APP processing by the nonamyloidogenic and amyloidogenic pathways is known in the art and reviewed, e.g., by Xu (2009) *J. Alzheimer's Dis.*, 16(2):211-224 and De Strooper et al., (2010) *Nat Rev Neurol.*, 6(2): 99-107.

One method to evaluate the efficacy of tropinol esters and related compounds described herein is to determine whether or not the compound(s) in question produce a reduction or elimination in the level of APP processing by the amyloidogenic pathway, e.g., a reduction or elimination in the level of APP processing by β-secretase cleavage. Assays for determining the extent of APP cleavage at the β-secretase cleavage site are well known in the art. Illustrative assays, are described, for example, in U.S. Pat. Nos. 5,744,346 and 5,942,400. Kits for determining the presence and levels in a biological sample of sAPPα and sAPPβ, as well as APPneo and Aβ commercially available, e.g., from PerkinElmer.

Cell Free Assays

Illustrative assays that can be used to evaluate the inhibitory activity of tropinol esters and/or related compounds described herein are described, for example, in PCT Publication Nos: WO 2000/017369, and WO 2000/003819, and in U.S. Pat. Nos. 5,942,400 and 5,744,346. In certain embodiments, such assays can be performed in cell-free incubations or in cellular incubations using cells expressing an alpha-secretase and/or beta-secretase and an APP substrate having an alpha-secretase and beta-secretase cleavage sites.

One illustrative assay, test the compound(s) of interest utilizing an APP substrate containing alpha-secretase and beta-secretase cleavage sites of APP, for example, a complete APP or variant, an APP fragment, or a recombinant or synthetic APP substrate containing the amino acid sequence: KM-DA or NL-DA, which is incubated in the presence of an α-secretase and/or β-secretase enzyme, a fragment thereof, or a synthetic or recombinant polypeptide variant having alpha-secretase or beta-secretase activity and effective to cleave the alpha-secretase or beta-secretase cleavage sites of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its α-secretase and/or β-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example, approximately 200 nanomolar to 10 micromolar substrate, approximately 10 to 200 picomolar enzyme, and approximately 0.1 nanomolar to 10 micromolar tropinol ester, in aqueous solution, at an approximate pH of 4-7, at approximately 37° C., for a time period of approximately 10 minutes to 3 hours. These incubation conditions are illustrative only, and can be varied as required for the particular assay components and/or desired measurement system. Optimization of the incubation conditions for the particular assay components can account for the specific alpha-secretase and/or beta-secretase enzyme used and its pH optimum, any additional enzymes and/or markers that might be used in the assay, and the like. Such optimization is routine and does not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of alpha-secretase and/or beta-secretase results in cleavage of the substrate at the alpha-secretase and/or beta-secretase cleavage sites, respectively. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assays

Numerous cell-based assays can be used to evaluate the effect of the compounds described herein on the ratio of relative alpha-secretase activity to beta-secretase activity and/or on the processing of APP to release amyloidogenic versus non-amyloidogenic Aβ oligomers. Contact of an APP substrate with an alpha-secretase and/or beta-secretase enzyme within the cell and in the presence or absence of compound(s) in question can be used to demonstrate α-secretase and/or β-secretase inhibitory activity of the compound(s). Preferably, the assay in the presence of compound(s) provides at least about 30%, most preferably at least about 50% inhibition of the enzymatic activity, as compared with a non-inhibited control.

In one illustrative embodiment, cells that naturally express alpha-secretase and/or beta-secretase are used. Alternatively, cells can be modified to express a recombinant α-secretase and/or β-secretase or synthetic variant enzymes, as discussed above. In certain embodiments, the APP substrate can be added to the culture medium and in certain embodiments, the substrate is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the α-secretase and/or β-secretase APP cleavage sites can be used, provided that the expressed APP is permitted to contact the enzyme and enzymatic cleavage activity can be analyzed.

Human cell lines that normally process Aβ from APP provide a useful means to assay inhibitory activities of the compound(s) described herein. Production and release of Aβ and/or other cleavage products into the culture medium can be measured, for example by immunoassay, such as Western blot or enzyme-linked immunoassay (EIA) such as by ELISA.

In certain embodiments, cells expressing an APP substrate and an active α-secretase and/or β-secretase can be incubated in the presence of the compound(s) being tested to demonstrate the effect of the compound(s) on relative enzymatic activity of the α-secretase and/or β-secretase as compared with a control. Relative activity of the alpha-secretase to the beta-secretase can be measured by analysis of one or more cleavage products of the APP substrate. For example, inhibition of β-secretase activity against the substrate APP would be expected to decrease release of specific β-secretase induced APP cleavage products such as Aβ, sAPPβ and APPneo. Promotion or enhancement of α-secretase activity against the substrate APP would be expected to increase release of specific α-secretase induced APP cleavage products such as sAPPα and p3 peptide.

Although both neural and non-neural cells process and release Aβ, levels of endogenous beta-secretase activity are low and often difficult to detect by EIA. The use of cell types known to have enhanced beta-secretase activity, enhanced processing of APP to Aβ, and/or enhanced production of Aβ are therefore preferred. For example, transfection of cells with the Swedish Mutant form of APP (APP-SW); with APP-KK (APP containing an ER retention signal (-KKQN-, (SEQ ID NO:1)) appended to the C terminus of APP), or with APP-SW-KK provides cells having enhanced beta-secretase activity and producing amounts of Aβ that can be readily measured.

In such assays, for example, the cells expressing APP, alpha-secretase and/or beta-secretase are incubated in a culture medium under conditions suitable for α-secretase and/or β-secretase enzymatic activity at its cleavage site on the APP substrate. On exposure of the cells to tropinol ester, the amount of Aβ released into the medium and/or the amount of CTF99 fragments of APP in the cell lysates is reduced as compared with the control. The cleavage products of APP can be analyzed, for example, by immune reactions with specific antibodies, as discussed above.

In certain embodiments, preferred cells for analysis of α-secretase and/or β-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze the effect of a tropinol ester or related compound described herein on the relative alpha-secretase and/or beta-secretase activity and/or processing of APP to release Aβ. For example, transgenic animals expressing APP substrate, alpha-secretase and/or beta-secretase enzyme can be used to demonstrate inhibitory activity of the tropinol ester or related compound. Certain transgenic animal models have been described, for example, in U.S. Pat. Nos. 5,877,399; 5,612,486; 5,387,742; 5,720,936; 5,850,003; 5,877,015, and 5,811,633, and in Games et al., (1995) *Nature* 373: 523-527. Preferred are animals that exhibit characteristics associated with the pathophysiology of AD. Administration of the tropinol ester or related compound to the transgenic mice described herein provides an alternative method for demonstrating the inhibitory activity of the compound(s) in question. In certain embodiments, administration of the tropinol ester or related compound in a pharmaceutically effective carrier and via an administrative route that reaches the target tissue in an appropriate therapeutic amount is preferred.

Inhibition of beta-secretase mediated cleavage of APP at the beta-secretase cleavage site and of Aβ release can be analyzed in these animals by measure of cleavage fragments in the animal's body fluids such as cerebral fluid or tissues. Likewise, promotion or enhancement of alpha-secretase mediated cleavage of APP at the alpha-secretase cleavage site and of release of sAPPα can be analyzed in these animals by measure of cleavage fragments in the animal's body fluids such as cerebral fluid or tissues. In certain embodiments, analysis of brain tissues for Aβ deposits or plaques is preferred.

In certain illustrative assays, an APP substrate is contacted with an alpha-secretase and/or beta-secretase enzyme in the presence of the tropinol ester and/or related compound under conditions sufficient to permit enzymatic mediated cleavage of APP and/or release of Aβ from the substrate. The tropinol ester and/or related compound is deemed effective when it reduces beta-secretase-mediated cleavage of APP at the β-secretase cleavage site and/or reduces released amounts of Aβ. The tropinol ester(s) and/or related compounds are also deemed effective if they enhance α-secretase-mediated cleavage of APP at the α-secretase cleavage site and to increase released amounts of sAPPα and/or to reduce Aβ deposition in brain tissues of the animal, and to reduce the number and/or size of beta amyloid plaques.

Methods of Monitoring Clinical Efficacy

In certain embodiments, clinical efficacy can be monitored using any method known in the art. Measurable biomarkers to monitor efficacy include, but are not limited to, monitoring blood, plasma, serum, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3 and decreased levels of sAPPβ and APPneo are indicators that the treatment or prevention regime is efficacious. Conversely, detection of decreased levels of sAPPα and/or p3, Aβ42 and increased levels of sAPPβ and APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including magnetic resonance imaging (MRI).

Efficacy can also be determined by measuring the cognitive abilities of the subject. Cognitive abilities can be measured using any method known in the art. One test is the clinical dementia rating (CDR) described above, while another is the mini mental state examination (MMSE) (Folstein, et al., *Journal of Psychiatric Research* 12 (3): 189-98). In certain embodiments, subjects who maintain the same score or who achieve a higher score on a CDR and/or on an MMSE indicate that the treatment or prevention regime is efficacious. Conversely, subjects who score lower on a CDR and/or on an MMSE indicate that the treatment or prevention regime has not been efficacious.

In certain embodiments, the monitoring methods can entail determining a baseline value of a measurable biomarker or parameter (e.g., amyloid plaque load or cognitive ability) in a subject before administering a dosage of tropinol ester or related compound, and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment, but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and a decision not to resume treatment can be considered/evaluated. In all of these cases, a significant difference relative to the control level (e.g., more than a standard deviation) is an indicator that resumption of the subject should be considered.

In certain embodiments, the tissue sample for analysis is typically blood, plasma, serum, mucous or cerebrospinal fluid from the subject.

EXAMPLES

The following examples are offered to illustrate, but not to limit the claimed invention.

Example 1

Synthesis of endo-8-methyl-8-azabicyclo[3.2.1]oct-3-yl 4-chlorobenzoate (Compound 5)

Figure 2:
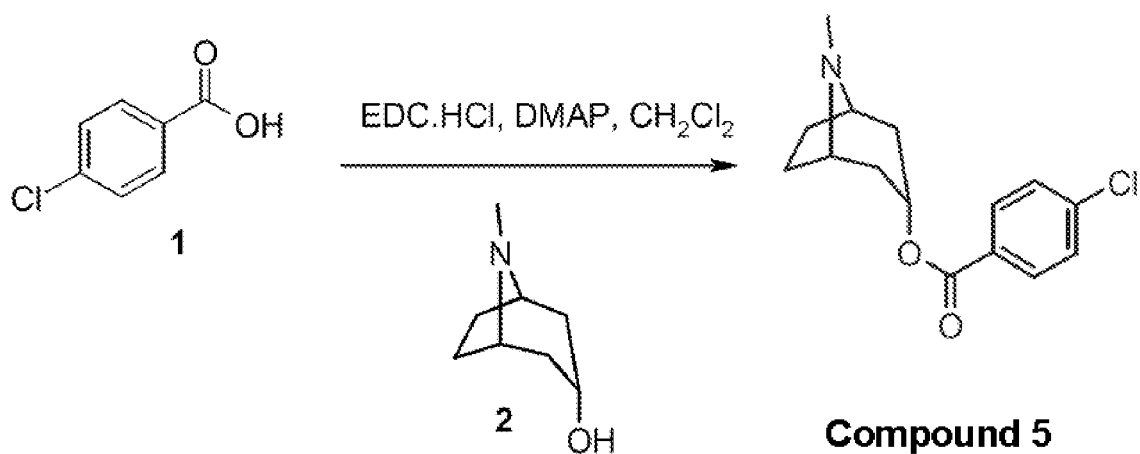
FIG. 2 illustrates Synthesis Scheme 1 for the synthesis of compound 5.

The synthesis of Synthesis of endo-8-methyl-8-azabicyclo[3.2.1]oct-3-yl 4-chlorobenzoate (Compound 5) is illustrated in Synthesis Scheme 1 (FIG. 2). To a solution of 4-chlorobenzoic acid, 1 (2.0 g, 12.77 mmol), EDC.HCl (6.1 g, 31.82 mmol) and DMAP (0.156 g, 1.277 mmol) in $CH_2Cl_2$ (15 mL) was added tropine, 2 (3.6 g, 25.5 mmol) in CH2Cl2 (5 mL) slowly at 0° C. After complete addition, the reaction mixture was brought to room temperature slowly and stirred for 16 h. The reaction was monitored with TLC. After completion, water was added (100 mL) and extracted with $CH_2Cl_2$ (3×50 mL). The organic layer was separated and washed with aqueous bisulfate (100 mL), water (100 mL) saturated brine (100 mL), dried over $Na_2SO_4$ and concentrated under vacuo. The crude product obtained was recrystallised with $CH_2Cl_2$ and pet ether to afford Cpd-5 (1.3 g, 36.4%) as a colorless solid.

Rf: 0.2 (20% MeOH in $CHCl_3$).
$^1$H-NMR (DMSO-$d_6$): δ 2.05-2.11 (m, 2H), 2.24 (bs, 4H), 2.55 (bs, 2H), 2.68 (bs, 3H), 3.84 (bs, 2H), 5.17 (bs, 1H), 7.65 (d, J=8.4 Hz, 2H), 7.97 (d, J=8.4 Hz, 2H), 10.26 (bs, 1H). LC-MS m/z: 280 [M+H]$^+$.

Example 2

Synthesis of endo-8-methyl-8-azabicyclo[3.2.1]oct-3-yl 2,3-dihydro-1,4-benzodioxine-6-carboxylate (Compound 7)

Figure 3:
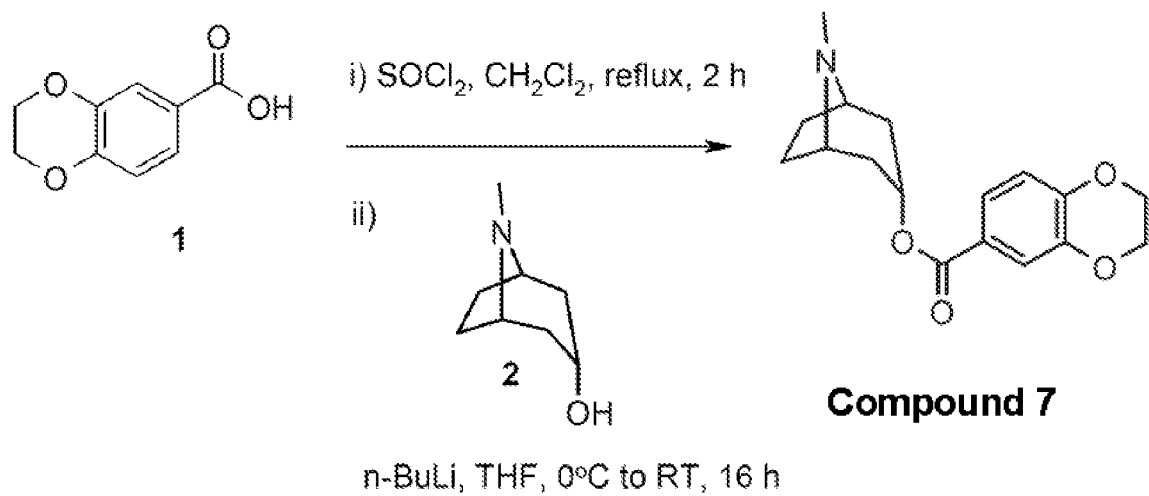
FIG. 3 illustrates Synthesis Scheme 2 for the synthesis of compound 7.

The synthesis of endo-8-methyl-8-azabicyclo[3.2.1]oct-3-yl 2,3-dihydro-1,4-benzodioxine-6-carboxylate (Compound 7) is illustrated in Synthesis Scheme 2 (FIG. 3). A solution of 1,4-benzodioxane-6-carboxylic acid, 1 (3.5 g, 19.43 mmol) in dichloromethane (35 mL) at room temperature under argon atmosphere was treated with thionyl chloride (35 mL, 479.83 mmol) and stirred for 3 h under reflux. The solution was then concentrated to leave the acid chloride as a dark black solid. The solid was then coevaporated with dichloromethane (2×25 mL) and dried under vacuum to remove the volatile impurities. The dark black solid was then dissolved in dry THF (35 mL). Meanwhile, on a separate flask, a solution of tropine, 2 (2.9 g, 20.54 mmol) in dry THF (30 mL) at 5° C. under argon atmosphere was treated with n-butyl lithium (0.5 M in hexanes, 20.6 mL, 10.27 mmol) and stirred for 30 min. at the same temperature. A solution of the acid chloride was added to the alkoxide solution at 5° C. dropwise. After completion of addition, the reaction mixture was allowed to warm to room temperature and stirred for another 16 h at the same temperature. The reaction was monitored with TLC. After completion, the reaction mixture was evaporated under vacuum. The residue was dissolved in dichloromethane (100 mL), washed with water (3×50 mL), saturated brine (50 mL), dried over $N_2SO_4$. The organic layer was filtered and evaporated under vacuum. The crude product was purified by flash column chromatography (neutral alumina) using a mixture of 80% EtOAc in pet ether as eluent to provide the product (2.3 g) as a pale yellow solid. The compound was further purified by recrystallisation using diethyl ether and n-hexanes to afford Cpd-7 (1.2 g, 20.36%) as a colorless solid.

Rf: 0.3 (30% MeOH in $CHCl_3$).
$^1$H-NMR (DMSO-d6): δ 1.63 (s, 1H), 1.68 (s, 1H), 1.87-2.09 (m, 6H), 2.17 (s, 3H), 3.03 (s, 2H), 4.28-4.33 (m, 4H), 5.04-5.07 (m, 1H), 7.00 (d, J=8.4 Hz, 1H), 7.38 (d, J=1.8 Hz, 1H), 7.45 (dd, J=8.4 Hz, 1.8 Hz, 1H).
LC-MS m/z: 304 [M+H]$^+$.

Example 3

Synthesis of (R)-Quinuclidin-3-yl 1H-indole-3-carboxylate (Compound 2)

Figure 4:
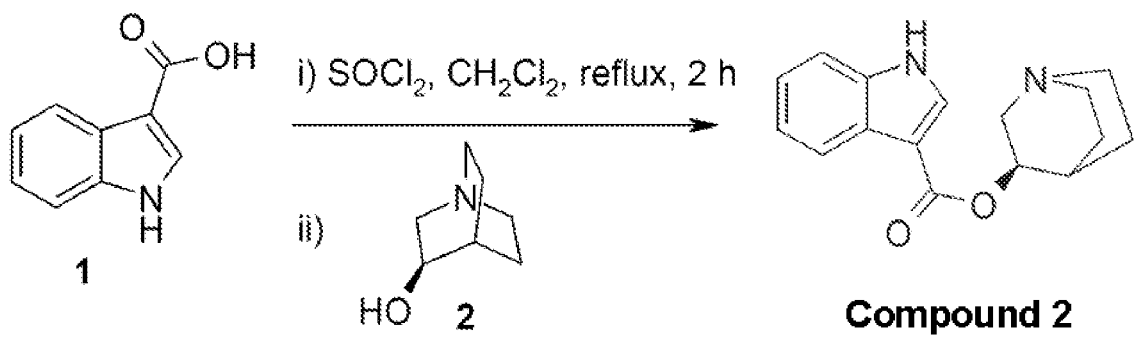
FIG. 4 illustrates Synthesis Scheme 3 for the synthesis of compound 2.

The synthesis of Synthesis of (R)-Quinuclidin-3-yl 1H-indole-3-carboxylate (Compound 2) is illustrated in Synthesis Scheme 3 (FIG. 4). A solution of indole-3-carboxylic acid, 1 (1.95 g, 12.10 mmol) in dichloromethane (19 mL) was treated with thionyl chloride (19 mL, 260.48 mmol) at room temperature under argon atmosphere and stirred for 2 h under reflux. The solution was then concentrated to leave the acid chloride as a dark brown solid. The solid was then co-evaporated with dichloromethane (2×25 mL) and dried under vacuum to remove the volatile impurities. The dark brown solid was then dissolved in dry THF (20 mL). In another RB flask, a solution of (R)-(−)-3-quinuclidinol, 2 (1.7 g, 13.4 mmol) in dry THF (17 mL) was treated with n-butyl lithium (0.5 M in hexanes, 13.3 mL, 6.65 mmol) at 0-5° C. under argon atmosphere and stirred for 30 min. at the same temperature. A solution of the acid chloride was added to the alkoxide solution at 5° C. dropwise. After completion of addition, the reaction mixture was allowed to warm to room temperature during which time a thick brown suspension was formed and stirred for another 16 h at room temperature. The reaction was monitored with TLC. After completion, the reaction mixture was evaporated under vacuum. The residue was dissolved in dichloromethane (100 mL), washed with water (3×50 mL), saturated brine (50 mL), dried over $Na_2SO_4$. The organic layer was filtered and evaporated under vacuum. The crude product was purified by flash column chromatography (neutral alumina) using a mixture of 4% MeOH in $CHCl_3$ as eluent to provide 1 g of 90% HPLC pure product. By following the same procedure from 2 g of indole carboxylic acid, 550 mg of 94.3% HPLC pure product was isolated. The two products were combined and recrystallised using IPA and n-hexane to give 0.85 g of 97.8% HPLC pure product. This was again purified by medium pressure column chromatography using MeOH in CHCl$_3$ (gradient 1% MeOH to 10% MeOH) to afford Cpd-2 (Lot-1: 0.470 g, 98.02% HPLC purity; Lot-2: 285 mg, 97.5% HPLC purity; 0.755 g, 11%) as a pale yellow solid.

R$_f$: 0.2 (30% MeOH in CHCl$_3$).

$^1$H-NMR (DMSO-d$_6$): δ 1.47-1.51 (m, 1H), 1.57-1.71 (m, 2H), 1.93-1.99 (m, 1H), 2.08-2.09 (m, 1H), 2.71-2.74 (m, 3H), 2.82-2.91 (m, 21-1), 3.24-3.41 (m, 1H), 4.94-4.96 (m, 1H), 7.17-7.23 (m, 2H), 7.47-7.50 (m, 1H), 7.98-8.01 (m, 1H), 8.12 (d, J=3 Hz, 1H), 11.97 (bs, 1H).

LC-MS m/z: 271 [M+H]$^+$.

Example 4

Synthesis of exo-8-Methyl-8-aza-bicyclo[3.2.1]octan-3-yl 1H-indole-3-carboxylate (Compound 4)

Figure 5:
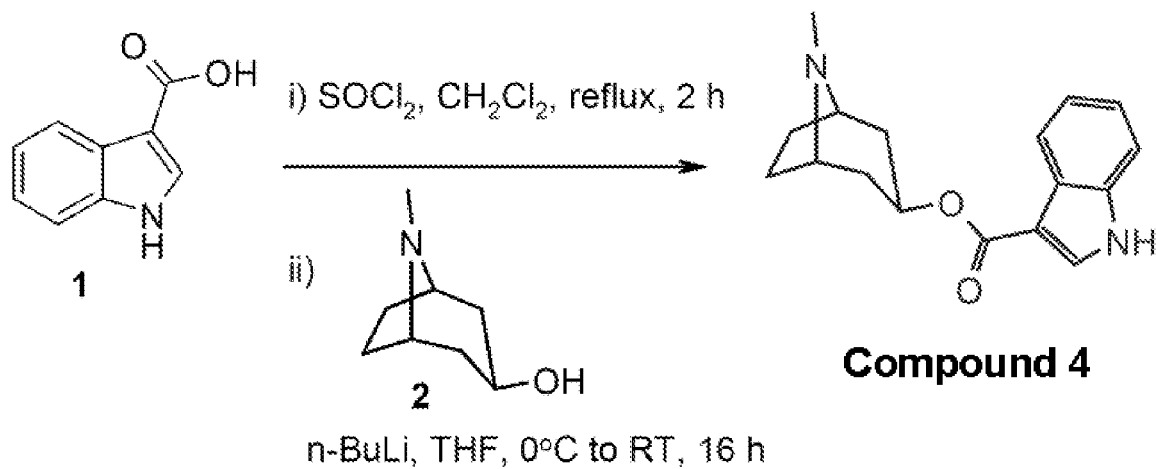
FIG. 5 illustrates Synthesis Scheme 4 for the synthesis of compound 4.

The synthesis of exo-8-methyl-8-aza-bicyclo[3.2.1]octan-3-yl 1H-indole-3-carboxylate (Compound 4) is illustrated in Synthesis Scheme 4 (FIG. 5). A solution of indole-3-carboxylic acid, 1 (1.5 g, 9.31 mmol) in dichloromethane (15 mL) at room temperature under argon atmosphere was treated with thionyl chloride (15 mL, 205.64 mmol) and stirred for 2 h under reflux. The solution was then concentrated to leave the acid chloride as a dark brown solid. The solid was then co-evaporated with dichloromethane (2×25 mL) and dried under vacuum to remove the volatile impurities. The dark brown solid was then dissolved in dry THF (15 mL). Meanwhile, on a separate flask, a solution of pseudotropine, 2 (1.45 g, 10.27 mmol) in dry THF (15 mL) at 5° C. under argon atmosphere was treated with n-butyl lithium (0.6 M in hexanes, 8.6 mL, 5.16 mmol) and stirred for 30 min. at the same temperature. A solution of the above acid chloride was added to the alkoxide solution at 5° C. dropwise. After completion of addition, the reaction mixture was allowed to warm to room temperature during which time a thick suspension was formed and stirred for another 16 h at room temperature. The reaction was monitored with TLC. After completion, the reaction mixture was evaporated under vacuum. The residue was dissolved in dichloromethane (100 mL), washed with water (3×50 mL), saturated brine (50 mL), dried over Na$_2$SO$_4$. The organic layer was filtered and evaporated under vacuum. The crude product was purified by flash column chromatography (neutral alumina) using a mixture of 4% MeOH in EtOAc as eluent to afford Cpd-4 (0.9 g, 34.0%) as a colorless solid.

R$_f$: 0.2 (20% MeOH in CHCl3).

$^1$H-NMR (CDCl$_3$): δ 1.82-1.89 (m, 2H), 2.05-2.21 (m, 6H), 2.52 (s, 3H), 3.38 (bs, 2H), 5.44-5.51 (m, 1H), 7.26-7.31 (m, 2H), 7.43-7.47 (m, 1H), 8.05 (s, 1H), 8.21-8.27 (m, 1H), 11.45 (bs, 1H).

LC-MS m/z: 285 [M+H]$^+$.

Example 5

Synthesis of endo-8-Methyl-8-azabicyclo[3.2.1]octan-3-yl-3,5-difluoro-1-benzyl-carboxylate (Compound 10)

Figure 7:
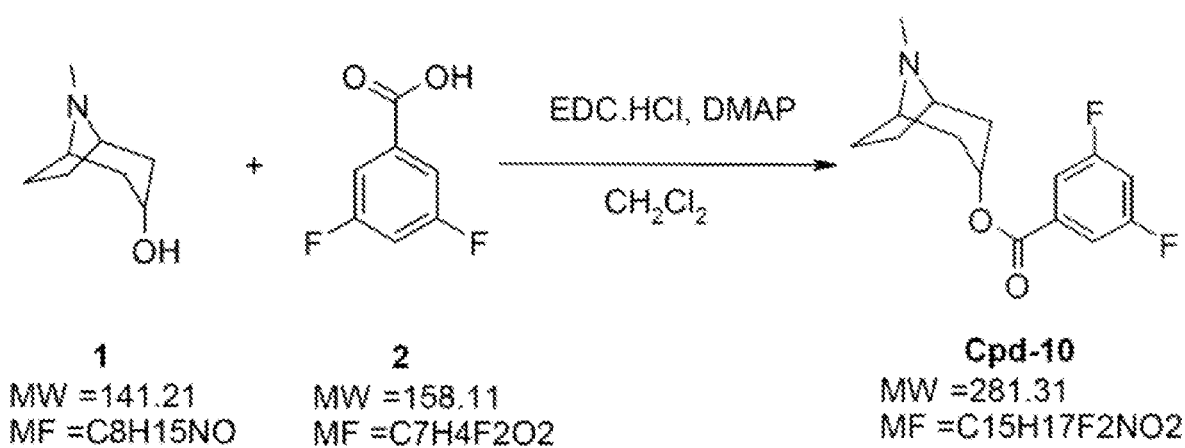
FIG. 7 illustrates Synthesis Scheme 6 for the synthesis of compound 10.

The synthesis of endo-8-Methyl-8-azabicyclo[3.2.1]octan-3-yl-3,5-difluoro-1-benzyl-carboxylate (Compound 10) is illustrated in Synthesis Scheme 6 (FIG. 7). To a solution of 3,5-difluorobenzoic acid, 2 (1.0 g, 6.33 mmol), EDC.HCl (2.67 g, 13.91 mmol) and DMAP (0.0773 g, 0.633 mmol) in CH2Cl2 (10 mL) was added tropine, 1 (1.07 g, 7.75 mmol) in CH$_2$Cl$_2$ (5 mL) slowly at 0° C. After complete addition, the reaction mixture was brought to room temperature slowly and stirred for 16 h. The reaction was monitored with TLC. After completion, water was added (100 mL) and extracted with CH2Cl2 (4×50 mL). The organic layer was separated and washed with aqueous bisulfate (100 mL), water (100 mL) saturated brine (100 mL), dried over Na$_2$SO$_4$ and concentrated under vacuo. The crude product obtained was recrystallised with CH$_2$Cl$_2$ and hexane to afford Cpd-10 (1.0 g, 56.2%) as a colorless solid.

Rf: 0.2 (20% MeOH in CHCl$_3$).

1H-NMR (300 MHz, CDCl3): δ 2.14-2.19 (m, 2H), 2.41 (bs, 4H), 2.82 (s, 3H), 3.19 (bs, 2H), 3.86 (bs, 2H), 5.42 (bs, 1H), 7.05-7.11 (m, 1H), 7.47-7.49 (m, 2H).

$^{13}$C-NMR (300 MHz, DMSO-d6): δ 164.51, 164.34, 163.35, 161.22, 161.05, 133.99, 133.87, 133.75, 112.97, 112.86, 112.73, 112.62, 109.85, 109.51, 109.17, 67.30, 60.87, 38.09, 33.81, 24.60.

LC-MS (m/z): 282 [M+H]$^+$.

HPLC: 99.64%.

Example 6

Synthesis of Compound 12

Figure 8:
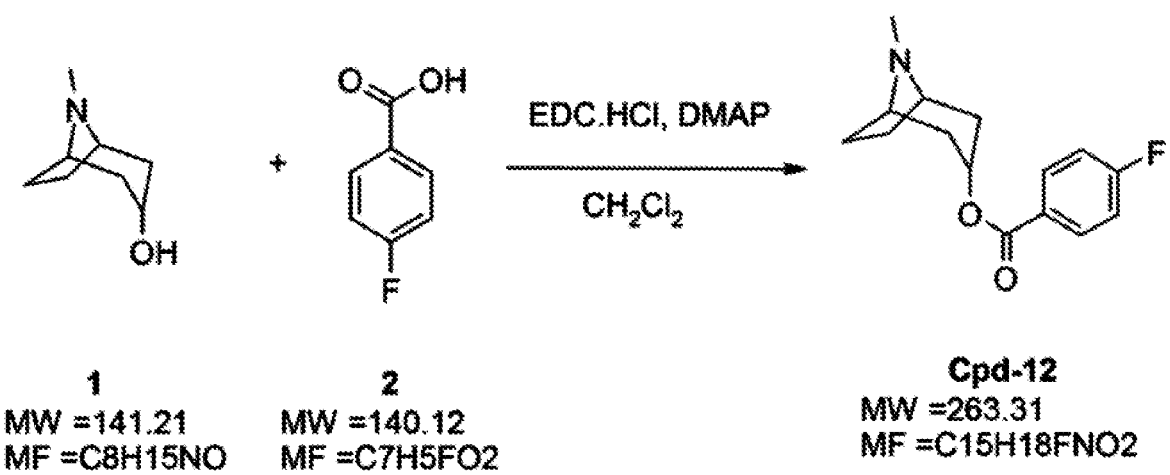
FIG. 8 illustrates Synthesis Scheme 7 for the synthesis of compound 12.

The synthesis of compound 12 is illustrated in Synthesis Scheme 7 (FIG. 8). To a solution of 4-fluorobenzoic acid, 2 (2.0 g, 14.27 mmol), EDC.HCl (6.02 g, 31.40 mmol) and DMAP (0.174 g, 1.43 mmol) in CH$_2$Cl$_2$ (20 mL) was added tropine, 1 (2.42 g, 17.13 mmol) in CH$_2$Cl$_2$ (10 mL) slowly at 0° C. After complete addition, the reaction mixture was brought to room temperature slowly and stirred. The reaction was monitored with TLC. After 16 h, water was added (100 mL) and extracted with CH$_2$Cl$_2$ (4×50 mL). The organic layer was separated and washed with aqueous bisulfate (2×100 mL), water (2×100 mL) saturated brine (100 mL), dried over Na$_2$SO$_4$ and concentrated under vacuo. The crude product was purified by flash column chromatography (Neutral alumina, Eluent: 0.5% MeOH in CH2Cl2) to afford Cpd-12 (1.2 g, 31.93%) as a colorless solid.

Rf: 0.2 (20% MeOH in CHCl$_3$).

1H-NMR (300 MHz, CDCl3): δ 1.86-1.91 (m, 2H), 2.06-2.2 (m, 4H), 2.32-2.39 (m, 5H), 3.26 (bs, 2H), 5.28 (t, J=5.1 Hz, 1H), 7.11-7.17 (m, 2H), 8.01-8.07 (m, 2H).

$^{13}$C-NMR (300 MHz, CDCl3): δ 167.47, 164.67, 164.10, 131.94, 131.82, 126.69, 126.66, 115.84, 115.55, 67.20, 60.53, 39.73, 35.72, 25.42.

LC-MS (m/z): 264 [M+H]$^+$.

HPLC: 98.85%

Example 7

Synthesis of Compound 9

Figure 6:
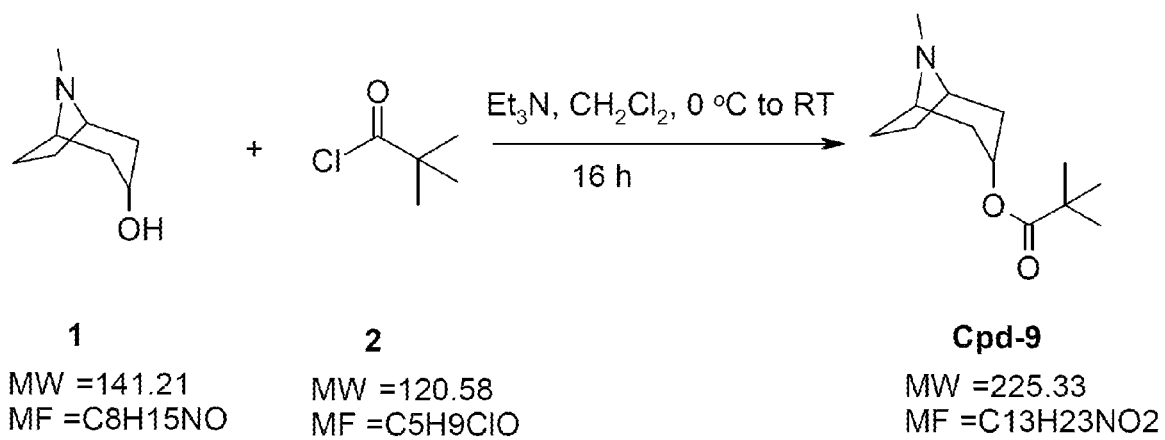
FIG. 6 illustrates Synthesis Scheme 5 for the synthesis of compound 9.

The synthesis of Compound 9 is illustrated in Synthesis Scheme 5 (FIG. 6). To a solution of tropine, 1 (2.0 g, 14.15 mmol) and triethylamine (2.4 mL, 16.98 mmol) in CH2Cl2 (20 mL) was added pivaloyl chloride, 2 (2.61 mL, 21.21 mmol) at 0° C. After complete addition, the reaction mixture was allowed to attain room temperature and stirred for 16 h. The reaction was monitored with TLC. After completion, water was added (50 mL) and extracted with CH2Cl2 (4×50 mL). The organic layer was separated, washed with saturated Na2CO3 (100 mL), water (100 mL) and saturated brine (100 mL). The organic layer was dried over Na$_2$SO$_4$ and concentrated under vacuo. The crude product was purified by flash column chromatography (Neutral alumina, Eluent: 5% MeOH in EtOAc) to afford Cpd-9 (1.8 g, 56.4%) as a pale yellow viscous liquid.

Rf: 0.2 (20% MeOH in CHCl$_3$).

1H-NMR (CDCl$_3$): δ 1.21 (s, 9H), 1.63-1.68 (m, 2H), 1.92-2.04 (m, 4H), 2.1-2.15 (m, 2H), 2.28 (s, 314), 3.10 (bs, 2H), 4.97 (t, J=5.1 Hz, 1H).

$^{13}$C-NMR (CDCl$_3$): δ 177.34, 66.86, 59.59, 40.26, 38.37, 36.48, 26.92, 25.47 LC-MS m/z: 226 [M+H]$^+$.

HPLC: 98.94%.

Example 8

Mouse Primary Neuronal Cell Testing

Figure 9:
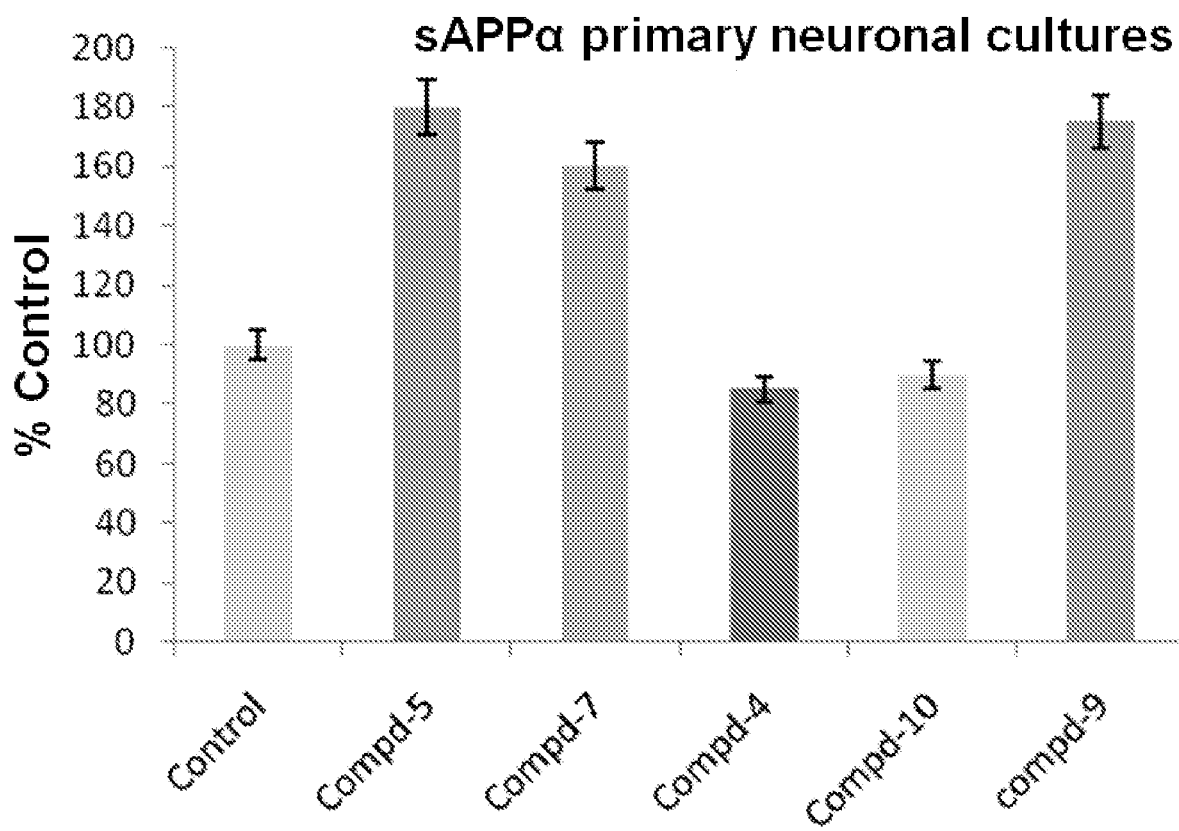
FIG. 9 illustrates sAPPα levels after treatment with various compounds.

Primary neuronal cultures were prepared from embryological day 18 embryos (E18) resulting from a male J20 to female J20 cross. The J20 mouse model of Alzheimer's Disease (AD) is a PDAPP model wherein human amyloid precursor protein (APP) with both the Swedish (KM670/671/NL) and Indiana (V717F) mutations is under the control of the platelet-derived growth factor promoter. The hippocampi from all embryos were combined, generating a culture with typically 75% transgenic cells. From a single litter, 9 wells on a 48 well plate were generated. The cultures, in Neurobasal with B27 supplement, glutamax, and penicillin/streptomycin, were allowed to mature for 4 days. One third of the media is changed every 3 days. Cells were treated once a day at 1 µM final drug concentration for 3 days. Before treatment started, an aliquot of media was saved from each well to use as "baseline" for comparison after treatment. On the last day, drug was added and cells and media collected 2 hours later. The readouts include sAPPalpha (AlphaLISA Perkin-Elmer), and Aβ1-42 (Invitrogen, sensitive ELISA kit) in media, and Aβ1-42 only in cells. When necessary to concentrate Abeta, samples were precipitated in methanol at −20° C. overnight and resuspended in a lesser volume of 5M guanidine HCl. The levels of sAPPα and Aβ were quantified from a standard curve and normalized to total cellular protein. sAPPα levels are shown in FIG. 9.

Example 9

Compound 14 Binding to APP Fragments

We used surface plasmon resonance to assess binding of compound 14 to the APP ectodomain (eAPP) fragments was done using a Biacore T100. Biotinylated TRX-eAPP575-624 and other eAPP fragments were immobilized onto strepavidin-coated sensor CM5 chip.

Figure 10:
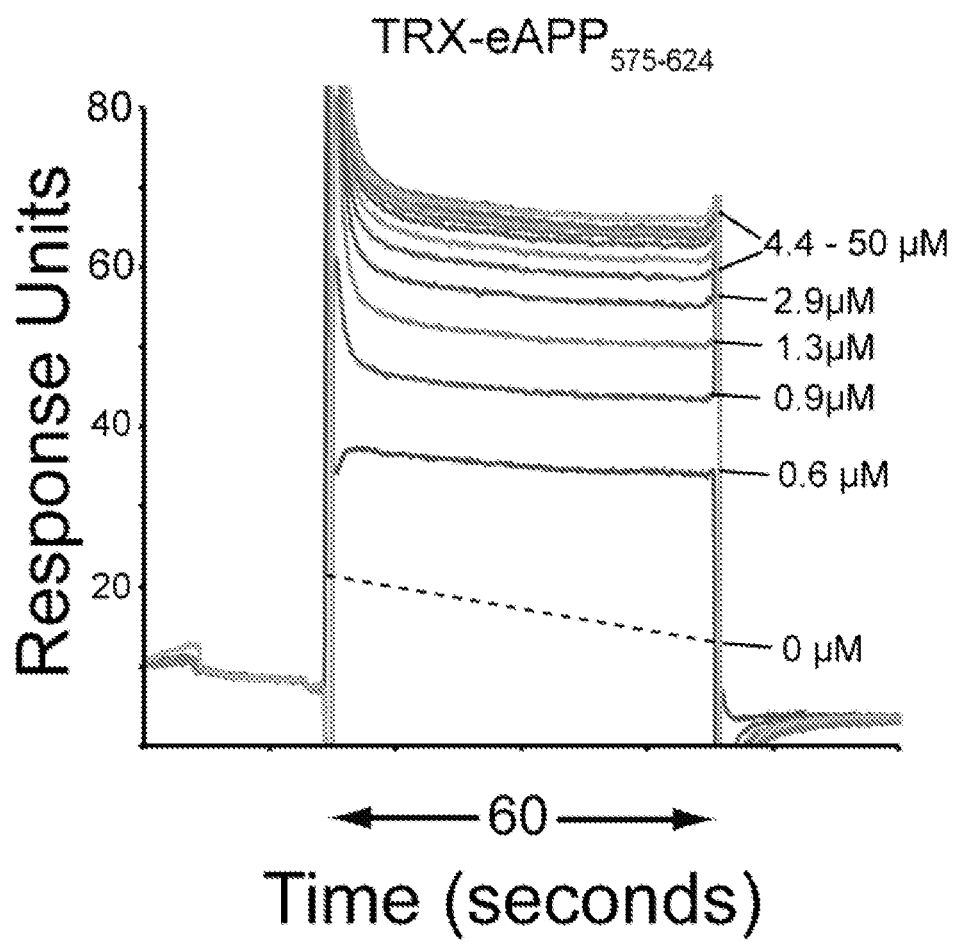
FIG. 10 illustrates BIACore results for compound 14 binding to TRX-eAPP$_{575-624}$.
Figure 11:
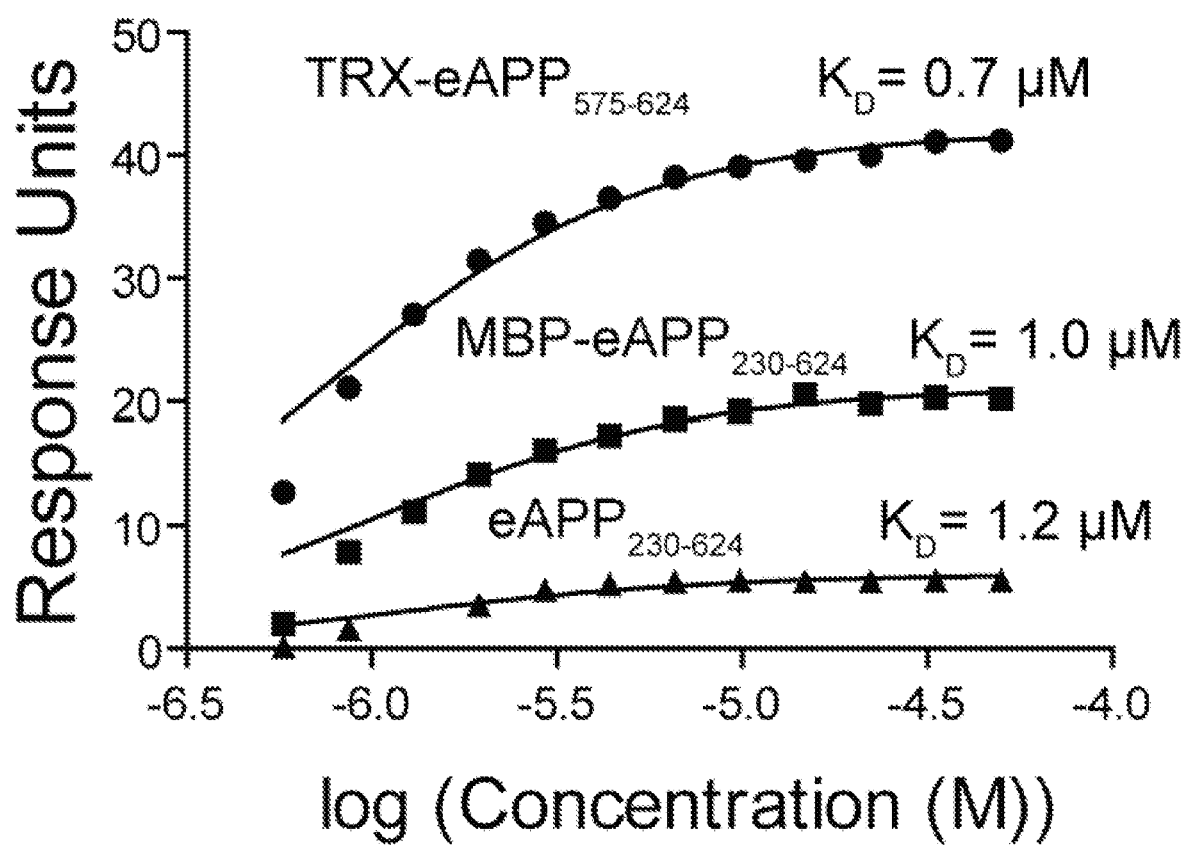
FIG. 11 illustrates binding of compound 14 to different fragments of APP.

Surface plasmon resonance data was obtained with a Biacore T100 for 0-50 µM compound 14 flowed at 1 µl per min in 1% DMSO, 20 mM sodium phosphate, 125 mM sodium chloride pH 7.4 over a CM5 chip cross-linked with proteins containing fragments of the ectodomain of APP$_{695}$. The three proteins were MBP-eAPP230-624—a fusion protein containing maltose binding protein and residues 230-624 of the ectodomain of APP (90-kDa), eAPP230-624—a protein that contains only residues 230-624 (45-kDa), and TRX-eAPP575-624—a fusion protein containing thioredoxin and residues 575-624 of the ectodomain (20-kDa). The proteins were produced as described in Libeu et al., (2011) J. Alzheimer's Dis., 25(3): 547-566. FIG. 10 shows the sensograms obtained with Trx-eAPP575-624. FIG. 11 compares the normalized response for the all three proteins. Comparison of the normalized curves between the proteins was done with PRISM (GraphPad Inc). The normalized curves were not significantly different when compared between the eAPP fragments suggesting that the binding site of compound 14 is between residues 575-624 of the ectodomain of APP.

The data indicate that compound 14 has affinity for APP and can directly bind to the ectodomain of APP supporting its role as a therapeutic and/or prophylactic agent (e.g., in the treatment or prophylaxis of an amyloidogenic pathology) as described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating Alzheimer's disease in a subject in need thereof with one or more risk factors for Alzheimer's disease, said method comprising:
administering to said subject a compound selected from the group consisting of

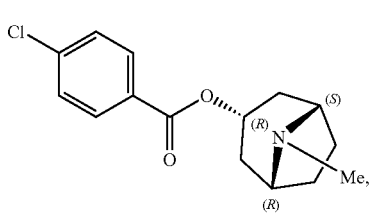

(Compound 5)

-continued (Compound 7)

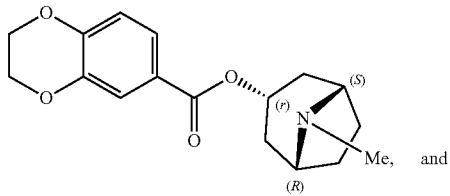

and (Compound 9)

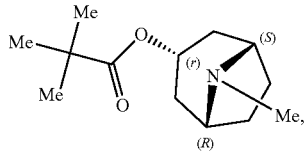

or a pharmaceutically acceptable salt, solvate, or hydrate thereof;

wherein said one or more risk factors are selected from the group consisting of a) said subject is a carrier of one or more apolipoprotein E (APOE) ε4 alleles and is AD-P biomarker positive, b) said subject is a carrier of an autosomal dominant mutation in one or more of APP, PS1, or PS2, and c) a combination thereof.

2. The method of claim 1, wherein said compound is:

(Compound 5)

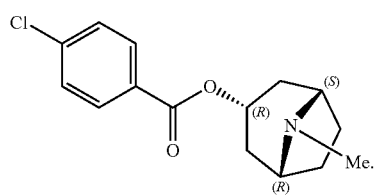

3. The method of claim 1, wherein said compound is:

(Compound 7)

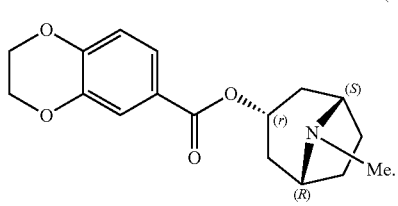

4. The method of claim 1, wherein said compound is:

(Compound 9)

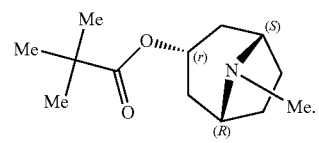

5. The method of claim 1, wherein said method produces a reduction in the CSF of said mammal of levels of one or more components selected from the group consisting of Tau, phospho-Tau (pTau), APPneo, soluble Aβ40 and soluble Aβ 42 and/or an increase in the CSF of levels of one or more components selected from the group consisting of Aβ42/Aβ40 ratio, Aβ42/Aβ38 ratio, sAPPα, βAPPα/βAPPβ ratio, βAPPα/Aβ40 ratio, and βAPPα/Aβ42 ratio.

6. The method of claim 1, wherein said method produces an increase in the CSF of said subject of sAPPα.

7. A method of treating Alzheimer's disease in a subject, said method comprising:

administering to the subject an amount of 1-1000 mg of a compound selected from the group consisting of (Compound 5)

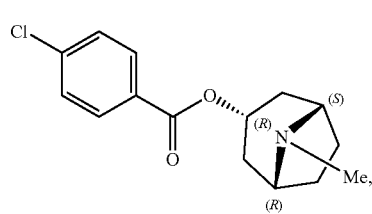

(Compound 7)

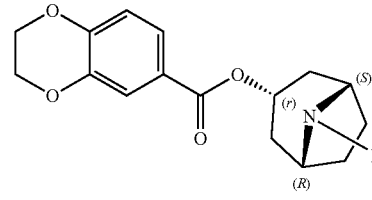

and (Compound 9)

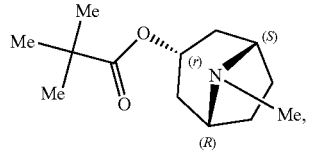

or a pharmaceutically acceptable salt, solvate, or hydrate thereof.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: artificial
<220> FEATURE:
<223> OTHER INFORMATION: ER retentionsignal peptide

<400> SEQUENCE: 1

Lys Lys Gln Asn
1
```